US012116560B2

(12) United States Patent
Yildirim-Ayan et al.

(10) Patent No.: US 12,116,560 B2
(45) Date of Patent: Oct. 15, 2024

(54) ADJUSTABLE GRAVITY SIMULATOR FOR TISSUE AND ORGAN CULTURING

(71) Applicant: The University of Toledo, Toledo, OH (US)

(72) Inventors: Eda Yildirim-Ayan, Toledo, OH (US); Halim Ayan, Toledo, OH (US); Charles Wade, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 18/588,750

(22) Filed: Feb. 27, 2024

(65) Prior Publication Data

US 2024/0200014 A1     Jun. 20, 2024

Related U.S. Application Data

(63) Continuation of application No. PCT/US2022/050364, filed on Nov. 18, 2022.

(60) Provisional application No. 63/307,277, filed on Feb. 7, 2022, provisional application No. 63/281,119, filed on Nov. 19, 2021.

(51) Int. Cl.
*C12M 1/42*     (2006.01)
(52) U.S. Cl.
CPC .................. *C12M 35/04* (2013.01)
(58) Field of Classification Search
CPC ..................................... C12M 1/264
USPC ....................................... 73/865.3
See application file for complete search history.

(56) References Cited

U.S. PATENT DOCUMENTS

| 3,270,441 A | 9/1966 | Hewes et al. |
| 5,848,899 A | 12/1998 | Howard |
| 9,194,977 B1 | 11/2015 | Dungan et al. |
| 9,430,953 B2 * | 8/2016 | Morris ................ G09B 9/04 |
| 2016/0103454 A1 | 4/2016 | Yuge et al. |
| 2016/0163218 A1 | 6/2016 | Chesi et al. |

FOREIGN PATENT DOCUMENTS

| WO | WO-2019202178 A1 * | 10/2019 | .............. B64G 7/00 |
| WO | WO-2022253466 A1 * | 12/2022 | .............. G09B 9/12 |

OTHER PUBLICATIONS

PCT International Search Report and Written Opinion, Application No. PCT/US22/50364, dated Feb. 16, 2023.

* cited by examiner

*Primary Examiner* — Octavia Hollington
(74) *Attorney, Agent, or Firm* — MacMillan, Sobanski & Todd, LLC

(57) ABSTRACT

Adjustable gravity simulators, mechanical loading devices, and methods for simulating gravitational loads and cell culturing are described. Further provided is an adjustable gravity simulator having a simulator chamber and a mechanical loading device configured to apply a mechanical load to samples in the simulator chamber while the simulator chamber experiences a microgravity or partial gravity simulation. Advantageously, the adjustable gravity simulator as described herein can address the challenges associated with cell culturing in simulated microgravity or partial gravity.

16 Claims, 24 Drawing Sheets
(7 of 24 Drawing Sheet(s) Filed in Color)

ADJUSTABLE GRAVITY SIMULATOR FOR TISSUE AND ORGAN CULTURING

RELATED APPLICATIONS

This is a continuation application of international application PCT/US2022/050364, filed under the authority of the Patent Cooperation Treaty on Nov. 18, 2022, published; which claims priority to U.S. Provisional Application No. 63/281,119 filed under 35 U.S.C. § 111(b) on Nov. 19, 2021, as well as U.S. Provisional Application No. 63/307,277 filed under 35 U.S.C. § 111(b) on Feb. 7, 2022. The entire disclosure of each of the aforementioned applications is expressly incorporated herein by reference for all purposes.

STATEMENT REGARDING FEDERALLY SPONSORED RESEARCH

This invention was made with no government support. The government has no rights in this invention.

BACKGROUND

As time goes on, humans are as focused as ever on the exploration of space. The rationale of such a profound goal lies in the potential for long-term colonization on planets besides Earth. Conducting early research on how humans can survive for long periods in space may become crucial for the future. The National Aeronautics and Space Administration's (NASA) "Artemis" program aims to reach the moon again by 2024, which is the first step to landing a human on Mars. This would require human astronauts to potentially live in space for years, something that has not been attempted to this day. Such an endeavor comes with perplexing problems including a lack of knowledge on how the human species adapts/reacts to the lunar, Martian, and low-orbit microgravity environments. Thus, understanding how mammalian and plant cells, tissues, and organs behave under various gravitational forces is a priority for space research programs.

Numerous studies conducted in simulated- and actual-microgravity environments have demonstrated that microgravity is associated with adverse tissue alterations. For instance, bone and muscle's hemostasis and structural integrities are affected by the absence of gravitational force. Space-associated osteopenia (bone loss at about 1-2% per month) and muscle atrophy (muscle loss ranging from 10-40%) pose great concerns in the short- and long-term space missions. Spaceflight studies have also demonstrated that microgravity decreases collagen fiber diameter and density within the musculoskeletal tissues, which leads to the destruction of chemical and structural tissue composition.

International Space Station (ISS)-National Laboratory is the only place currently providing the unique and unparalleled research environments of space and microgravity. Yet, it is impossible to carry all the microgravity-related studies at the ISS. Thus, simulating microgravity on Earth is very important to investigate how microgravity affects tissue regeneration, hemostasis, and drug efficacy.

Currently, two-dimensional (2D) clinostat, rotating wall vessels (RWV), and random positioning machines (RPM) are used to create a microgravity-like environment on Earth. The 2D clinostat rotates with one rotation axis running perpendicular to the gravity vector direction and prevents the biological system from perceiving the gravitational acceleration vector. It is primarily used in plant research or single cell-based experiments, so it is not suitable for 3D tissue culture experiments. RWVs are another type of platform developed by NASA for studying cell cultures and aquatic organisms such as zebrafish eggs/embryos. The organism of interest is cultured in suspension within a container mounted on a horizontal plane and rotating on one axis with a variable speed perpendicularly to the direction of the Earth gravity vector. The cells or cell aggregates are cultured in suspension with a continuous low shear and low turbulence environment that is similar to the space microgravity environment. There are several analogs of RWV including rotating wall bioreactors (RWBs), rotating cell culture systems (RCCSs), and high aspect rotating vessels (HARVs). In principle, they all work with similar physical principles but using different configurations. However, it is not possible to mimic the physiologically relevant compression, tensile, and biaxial mechanical loading to the cells and cell aggregates using RWVs and their analogs, since only low shear can be applied using these platforms.

It should be noted that the magnitude of the Earth gravity vector cannot be altered using the microgravity simulation platforms, but the effect of Earth gravity on the subject can be changed. Among these microgravity simulating platforms, random positioning machines minimize the effect of the Earth gravity vector more effectively compared to 2D clinostats and RWVs. In RPMs, the effectiveness of minimizing Earth gravity is achieved by rotating the subject around two axes using two independently rotating frames that can be operated under variable speeds and directions. However, the majority of RPMs can only accommodate cell-culture plates or Petri dishes in which cells are cultured in monolayer (2D) form. Thus, culturing 3D tissues or organs is not possible within these platforms. Further, without exception, current microgravity simulating platforms cannot apply pre-defined mechanical strain and frequency on cultured cells. They operate under static cell culture conditions in which cells are cultured within a cell culture media without mechanical stimulation. Yet, it is well-established that mimicking the dynamic mechanical environment around the tissue of interest is very important to create reliable in vitro tissue models.

The tissues in vivo residing in a mechanically active environment experience forms of tensile micromechanical strains, hydrostatic cyclic pressure, and compressive strains depending on the type of tissue. For instance, bones are primarily under compression loading, however, within the bone tissue, osteocytes are under fluid flow stress. Muscles normally experience a tensile stretch in vivo with a range of 5-15% from moderate to vigorous physical activities. In walking, leg muscles are uniaxially stretched to 5-9% strain, and during sprinting the uniaxial strain in muscle is 12%. Tendons and ligaments also experience uniaxial strain with a range of 5-16%. The cartilage tissue is primarily subjected to compressive loads and hydrostatic pressure but can experience shear at the surface layer as well. The human myocardium undergoes biaxial mechanical strains ranging from 5% to 25% in all segments (apical, middle, basal) with almost 1 Hz frequency (72 rpm) for 24 hours. Myocardial strain measurements taken from tagged magnetic resonance imaging (MRI) demonstrated that circumferential strain values were $-23\pm4\%$, $-22\pm3\%$, $-16\pm5\%$, and $-16\pm4\%$ in the anterior, lateral, inferior, and septal sectors of an equatorial slice, respectively.

Experiencing the aforementioned mechanical strains with proper frequency is very important for tissue health. There is an overwhelming amount of evidence suggesting that the mechanical environment around the tissues affects the hemostasis, regeneration, and disease state of the tissues. For instance, in the abdominal wall region, the mechanical strain in the context of stretching also induces changes in the response of cells residing in the peritoneal cavity. In the absence of mechanical loading, the tendon loses its strength, modulus, toughness, and collagen alignment. A study using a mouse model in which the shoulder was paralyzed (no mechanical loading) demonstrated that enthesis tissue was deformed and mineralization was decreased in the bone insertion site. While the mechanical environment is such a dominant factor in tissue hemostasis, it needs to be considered and replicated in 3D in vitro tissue models for tissue regeneration and drug development studies conducted on Earth and microgravity environment. Yet, there is no microgravity simulation platform or mechanical loading platform that can simulate the microgravity effectively while culturing the 3D tissue-like structure under physiologically relevant mechanical strain and frequency.

There remains a need in the art for new and improved adjustable gravity simulators, especially for cell culturing.

SUMMARY

Provided is an adjustable gravity simulator comprising a simulator chamber configured to house a sample and rotate independently around a first axis and a second axis; a rotating arm rotatably connected to a mount and having side members extending toward the simulator chamber, wherein rotation of the rotating arm around the first axis in turn causes rotation of the simulator chamber around the first axis; a belt tensioner on one of the side members and connected to the simulator chamber, wherein the belt tensioner comprises a belt configured to move in a loop thereby driving the rotation of the simulator chamber around the second axis; and one or more motors configured to drive (i) the rotation of the rotating arm around the first axis, and thereby the rotation of the simulator chamber around the first axis, and (ii) movement of the belt in the loop, and thereby the rotation of the simulator chamber around the second axis.

In certain embodiments, the one or more motors comprises a first motor configured to drive the rotation of the rotating arm relative to the mount, and a second motor configured to drive the movement of the belt in the loop.

In certain embodiments, the adjustable gravity simulator further comprises a control module configured to control the one or more motors.

In certain embodiments, the mount comprises a wheel and a cable, wherein rotation of the wheel by movement of the cable causes corresponding rotation of the rotating arm around the first axis, and wherein movement of the cable is driven by a first motor.

In certain embodiments, the mount is disposed on a base defining a surface and extends orthogonally from the surface.

In certain embodiments, the adjustable gravity simulator further comprises a second motor configured to drive rotation of an arm wheel in the loop, and thereby drive movement of the belt in the loop, rotation of the chamber wheel, and rotation of the simulator chamber around the second axis.

In certain embodiments, the adjustable gravity simulator further comprises a mechanical loading device within the simulator chamber, wherein the mechanical loading device is configured to apply a mechanical load to a sample housed therein. In particular embodiments, the adjustable gravity simulator further comprises one or more slip rings configured to provide electricity to the mechanical loading device within the simulator chamber. In particular embodiments, the mechanical loading device comprises a loading chamber configured to house a sample and a third motor configured to apply a mechanical load to the sample in the loading chamber. In particular embodiments, the third motor is configured to move the sample axially along a third axis in a back-and-forth manner. In particular embodiments, the mechanical loading device comprises a loading plate configured to receive and support a sample or culturing chamber, and the mechanical loading device further comprises a third motor configured to move the loading plate axially along a third axis in a back-and-forth manner.

In certain embodiments, movement of the belt in the loop drives rotation of a chamber wheel, and rotation of the chamber wheel in turn drives rotation of the simulator chamber around the second axis.

In certain embodiments, the side members extend from a side of the rotating arm opposing the mount and facing the simulator chamber.

In certain embodiments, the adjustable gravity simulator further comprises an accelerometer configured to collect gravitational data.

In certain embodiments, the adjustable gravity simulator comprises a first motor and a second motor, wherein the first motor is configured to drive movement of a cable around a wheel which causes corresponding rotation of the rotating arm around the first axis, and thereby drives rotation of the simulator chamber around the first axis; and the second motor is configured to drive movement of the belt in the loop, and thereby drive rotation of an arm wheel in the loop which, in turn, causes corresponding rotation of the simulator chamber around the second axis.

Further provided is an adjustable gravity simulator comprising a simulator chamber configured to be rotated around two axes in a controlled manner so as to subject a sample within the simulator chamber to a reduced average g-force so as to simulate microgravity or partial gravity; and a mechanical loading device in the simulator chamber, wherein the mechanical loading device is configured to apply a mechanical load to the sample while the sample experiences a microgravity or partial gravity simulation within the simulator chamber.

Further provided is a method of simulating microgravity or partial gravity, the method comprising rotating a sample around a first axis at a first speed and in a first orientation; rotating the sample around a second axis at a second speed and in a second orientation; and applying a mechanical load to the sample while rotating the sample around the first axis and around the second axis; wherein the rotation around the first axis is simultaneous to the rotation around the second axis; and wherein the first speed, first orientation, second speed, and second orientation are capable of being varied independently of each other so as to achieve a reduced average g-force experienced by the sample while the mechanical load is being applied to the sample.

In certain embodiments, the method further comprises collecting gravitational data with an accelerometer while rotating the sample around the first axis and the second axis, and using the collected gravitational data to verify a partial gravity or microgravity simulation on the sample.

In certain embodiments, the method further comprises controlling the rotation around the first axis and the second axis through a control module having a graphical user interface and configured to accept inputted information relating to gravitational data, mechanical loading strain, or mechanical loading frequency.

In certain embodiments, the first speed is constant and the second speed is constant.

In certain embodiments, the first orientation and the second orientation are inverted at random intervals to create a unique path that guarantees that no particular orientation is visited more than others, thereby causing the sample to experience a microgravity simulation.

In certain embodiments, the first speed or the second speed is biased so that at least one orientation is visited more than others, thereby causing the sample to experience a partial gravity simulation.

Further provided is an adjustable gravity simulator having a simulator chamber and a mechanical loading configured to apply a mechanical load to samples in the simulator chamber while the simulator chamber experiences a microgravity or partial gravity simulation.

Advantageously, the adjustable gravity simulator as described herein can address the challenges associated with cell culturing in simulated microgravity or partial gravity. Desirably, the adjustable gravity simulator can provide versatile culturing conditions (2D monolayer, cell-laden 3D tissue constructs, and ex-vivo organ culture) under physiologically relevant mechanical strain and frequency loading.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

As used herein, the term "microgravity" generally refers to weightlessness and zero-g, but with the understanding that g-forces are never exactly zero; rather, g-forces can be very small. For example, the International Space Station (ISS), which is located in low-earth orbit, experiences small g-forces from tidal effects, gravity from objects other than Earth, such as astronauts, the spacecraft, the Sun, air resistance, and astronaut movements that impart momentum to the space station.

As used herein, the term "partial gravity" generally refers to any g level between theoretical zero up to Earth's gravity. For example, the acceleration due to gravity on the surface on the Moon is about 16.6% of that on Earth's surface or 0.166 g.

Referring now to FIGS. 1-3, 9-10, an adjustable gravity simulator 100 has a simulator chamber 102 and a mount 104. As seen in FIGS. 1-3, 9-10, the mount 104 may have a generally triangular shape, however this is not strictly necessary. FIGS. 9-14 illustrate different views of the adjustable gravity similar 100, according to one embodiment. The simulator chamber 102 is configured to receive one or more samples. Non-limiting examples of the samples include organisms, cell-laden tissue scaffolds, 3D tissues, and/or organs, such as intervertebral discs. Advantageously, whereas most experiments studying human diseases utilize two-dimensionally cultured cell lines, which do not mimic the real tissue environment, the adjustable gravity simulator 100 can be used in connection with three-dimensional tissues. In other words, the adjustable gravity simulator 100 can culture three-dimensional tissues and organs in altered gravity conditions. It should be appreciated that a skilled artisan may select other biological and non-biological materials for the samples, as desired. For example, the simulator chamber 102 may be large enough to accommodate a living organism, such as a mouse or a human.

Figure 1:
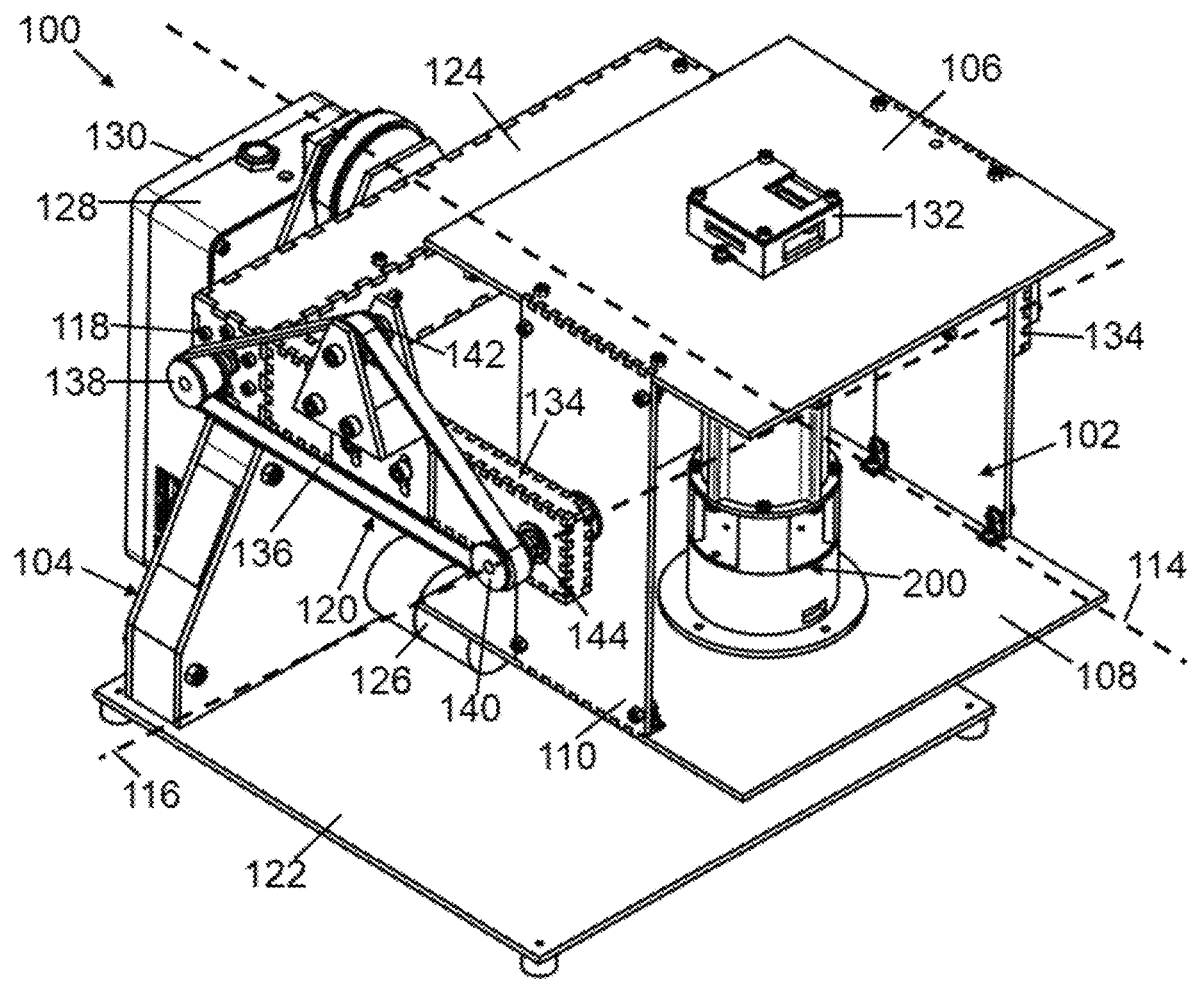
FIG. 1: Top perspective view of a non-limiting example of an adjustable gravity simulator.
Figure 2:
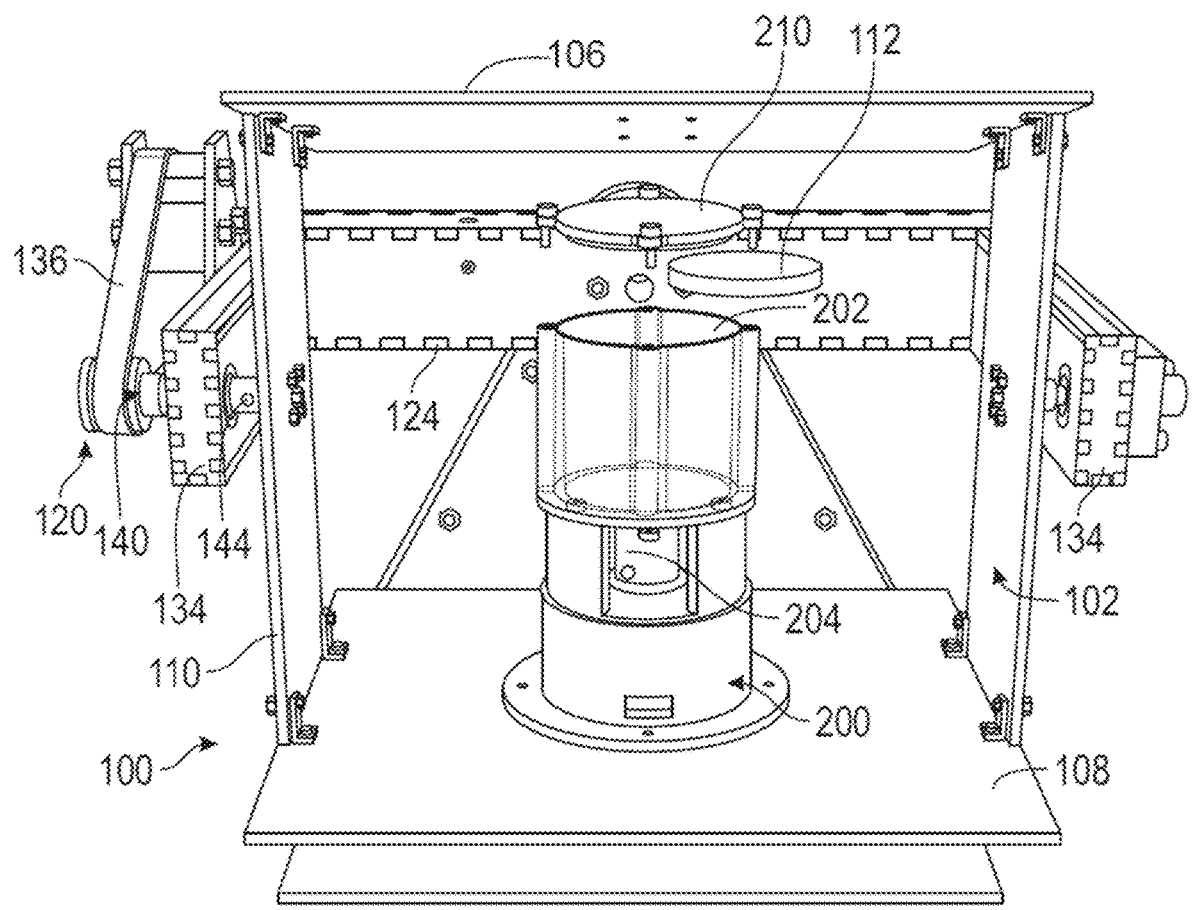
FIG. 2: Front perspective view of the adjustable gravity simulator shown in FIG. 1 with a culturing chamber shown removed from a mechanical loading device in the simulator chamber. The mechanical loading device is shown with the lid open.
Figure 3:
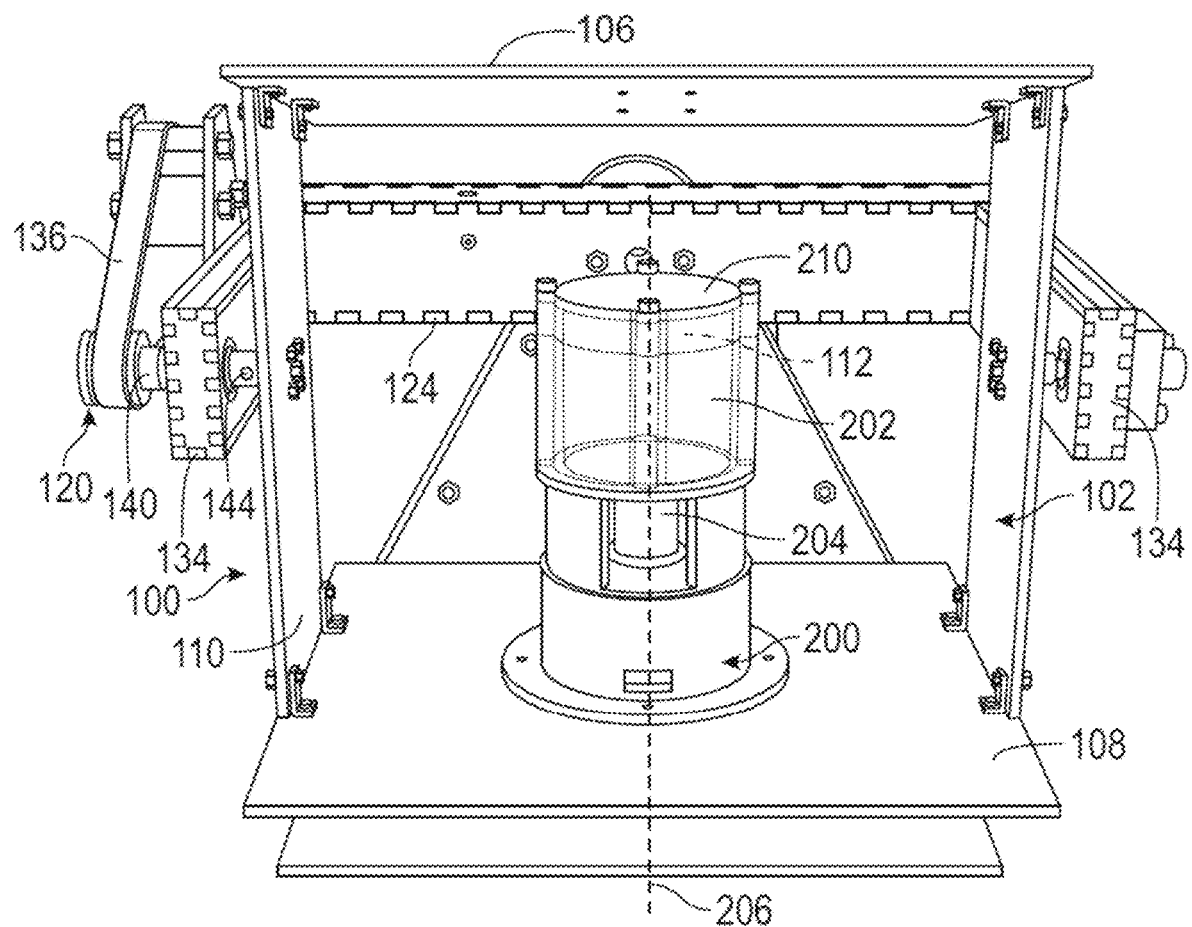
FIG. 3: Front perspective of the adjustable gravity simulator shown in FIG. 1 with the culturing chamber loaded into the mechanical loading device.
Figure 4:
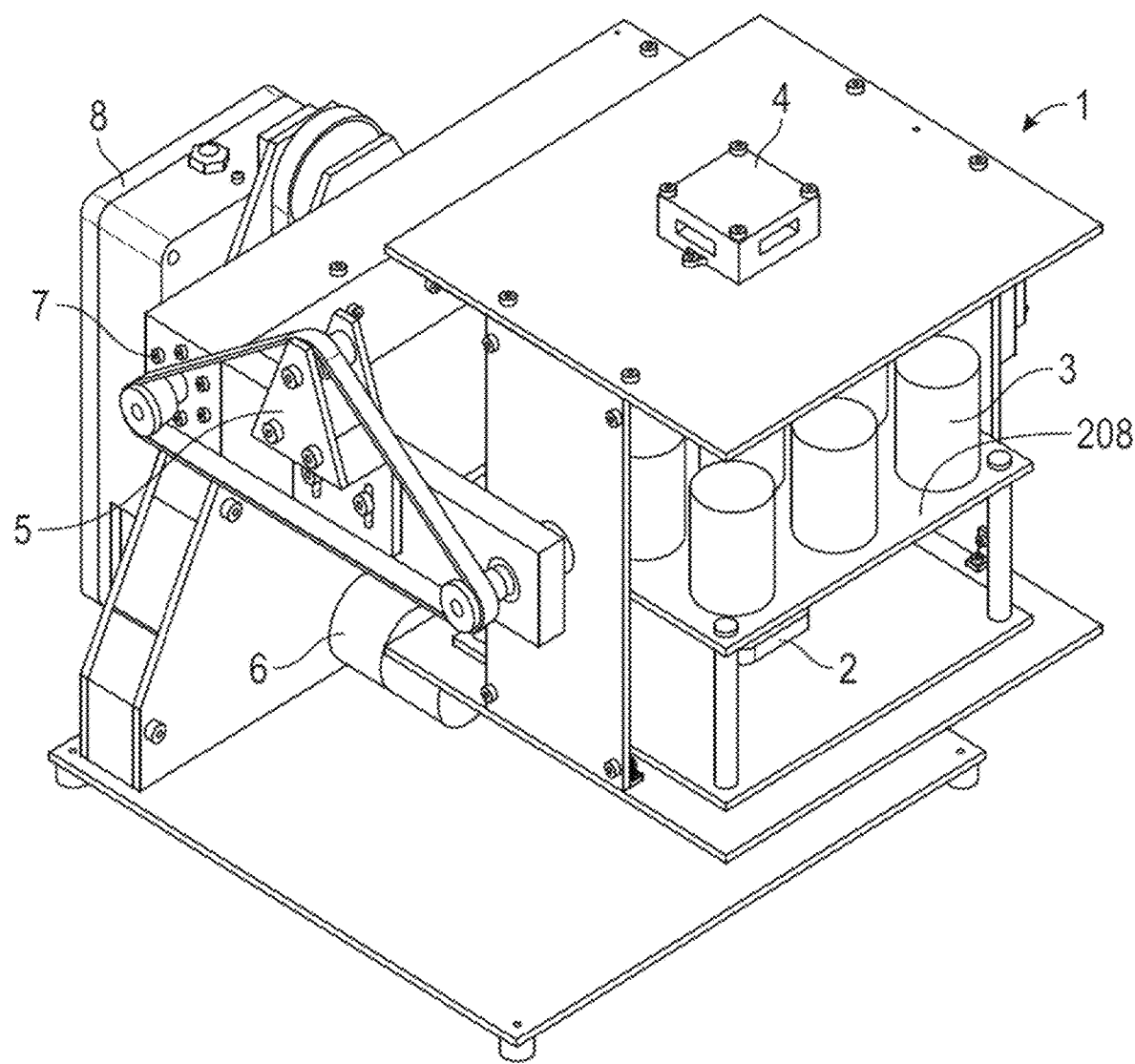
FIG. 4: Top perspective view of another non-limiting example of the adjustable gravity simulator.

Referring now to FIGS. 1-3, 11-12, the simulator chamber 102 may have a first plate 106 and a second plate 108 connected by side wall members 110. The simulator chamber 102 may include any number of side wall members 110, depending on the desired degree of enclosure. One or more samples to be subjected to a microgravity or partial gravity simulation may be disposed between the first plate 106 and the second plate 108. The samples may be mounted or affixed to the first plate 106 and/or the second plate 108. As shown in FIG. 2, the simulator chamber 102 may include one or more culturing chambers 112. Each of the culturing chambers 112 is a container configured to house samples such as cells in a suitable culturing medium. Each of the culturing chambers 112 may be interchangeable with culturing chambers 112 of different shapes and/or sizes. Advantageously, this allows the adjustable gravity simulator 100 to accommodate different types and sizes of the samples. For example, the sample may include an intervertebral disc (IVD), tendon, bone, cartilage, or muscle. It should be appreciated that the size and shape of the culturing chambers 112 may be adjusted according to the size and shape of the samples, for example as shown in FIG. 4. Furthermore, any number of culturing chambers 112 may be disposed within the simulator chamber 102.

Referring now to FIG. 1, the simulator chamber 102 is configured to rotate around two axes in order to create the microgravity or partial gravity simulation. The simulator chamber 102 may be configured to rotate around a first axis 114 and rotate around a second axis 116 independently and at independent speeds. The first axis 114 may be substantially perpendicular to the second axis 116, although this is not strictly necessary. Desirably, and as will be described in further detail below, the rotation of the simulator chamber 102 around the first axis 114 and the second axis 116 can permit the simulator chamber 102 to experience a microgravity or partial gravity simulation. This rotation may be accomplished using a variety of methods and technologies. For example, the adjustable gravity simulator 100 may have a first motor 126 that is configured to drive the first simulator chamber 102 to rotate around the first axis 114, and a second motor 118 configured to drive the simulator chamber 102 to rotate around the second axis 116, as described in more detail below. The first motor 126 may be disposed on the base 122, and the second motor 118 may be disposed within a rotating arm 124. However, other locations for the first motor 126 and the second motor 118 are possible and encompassed within the scope of the present disclosure. In addition, the adjustable gravity simulator 100 may have a belt tensioner 120, as shown in FIGS. 1-3. The belt tensioner 120 is in communication with the second motor 118 and the simulator chamber 102. The belt tensioner 120 is configured to transfer the rotational force generated by the second motor 118 to the simulator chamber 102, so as to cause the simulator chamber 102 to rotate around the second axis 116. It should be appreciated that other methods and technologies may be employed to drive the simulator chamber 102 to rotate around the first axis 114 and the second axis 116, within the scope of this disclosure.

Figure 11:
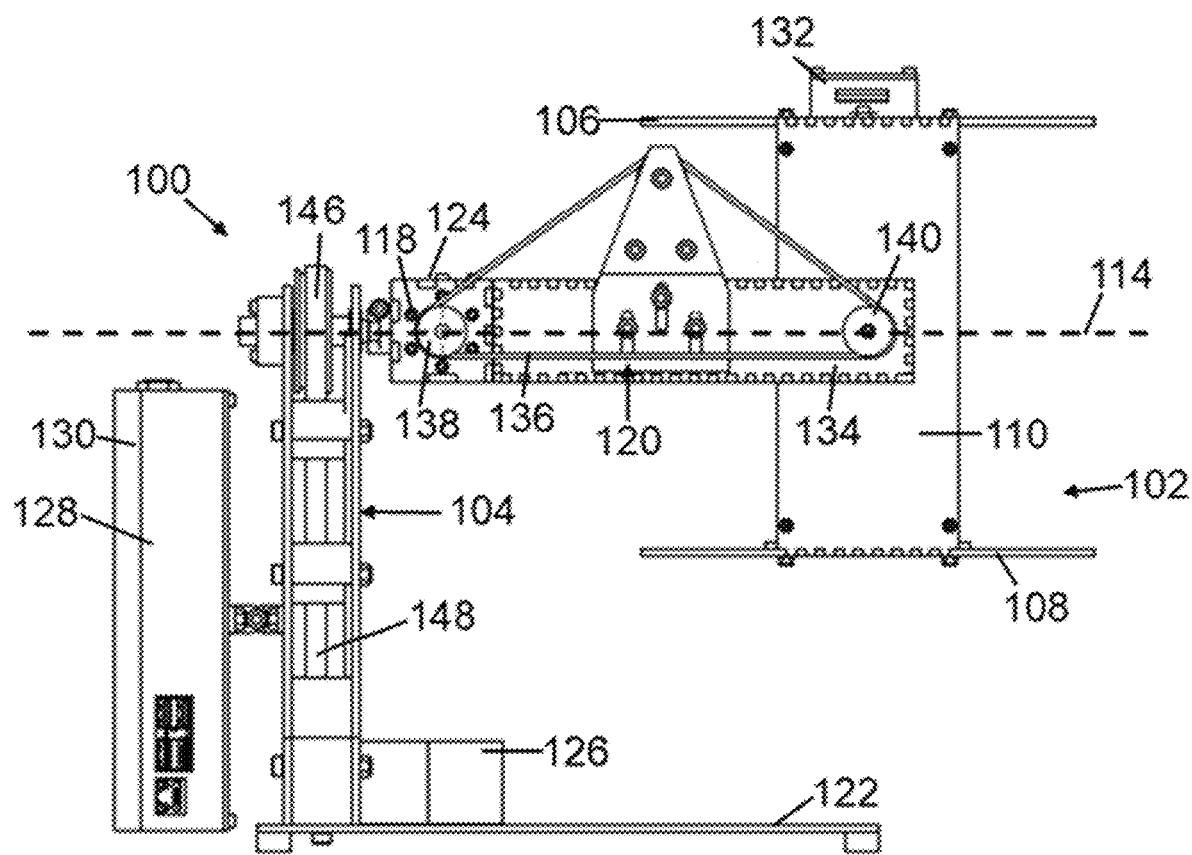
FIG. 11: Left elevational view of the adjustable gravity simulator shown in FIG. 9.
Figure 12:
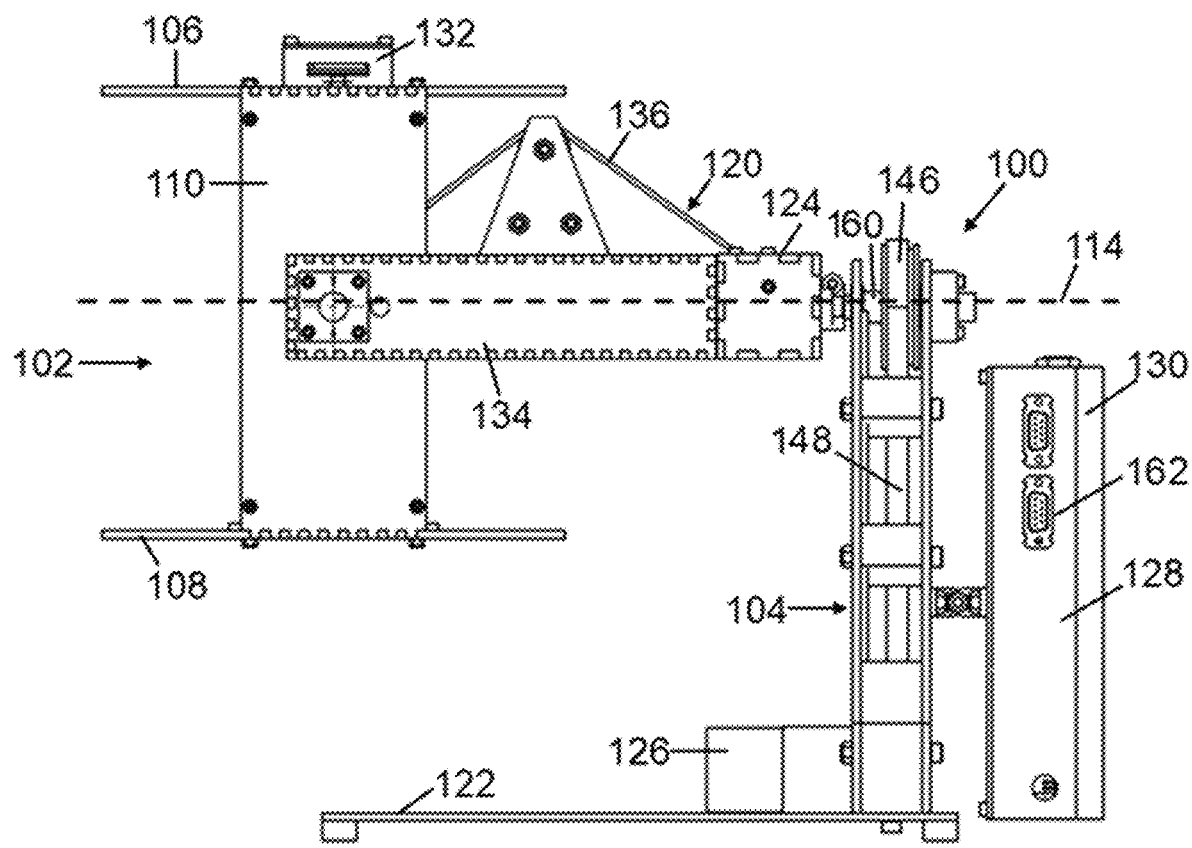
FIG. 12: Right elevational view of the adjustable gravity simulator shown in FIG. 9.

Referring still to FIGS. 1, 11-12, the mount 104 is connected to the simulator chamber 102 by the rotating arm 124 that allows the simulator chamber 102 to rotate around the first axis 114 while the mount 104 remains stationary. The rotating arm 124 includes two side members 134 which connect the simulator chamber 102 to the rotating arm 124 on opposing sides of the simulator chamber 102. The side members 134 extend from a side of the rotating arm 124 opposing the mount 104 and facing the simulator chamber 102. The side members 134 extend in a direction toward the simulator chamber 102. As described in more detail below, the simulator chamber 102 may rotate within the two side members 134.

As best seen in FIGS. 11-12, the mount 104 may include a wheel 146 which is driven by the first motor 126 through a cable 148 within the mount 104. The mount 104 may be disposed on a base 122 which may be in the form of a platform that is configured to remain stationary and provide support to the mount 104. The mount 104 rests on the base 122, and may extend upward from the base 122 in a generally orthogonal manner. The first motor 126 may also rest on the base 122 adjacent to the mount 104, and in communication with the cable 148. The wheel 146 may be housed at the top of the triangular mount 104, with the cable 148 running around the wheel 146 and down the sides of the mount 104 to the first motor 126, which may be disposed on the base 122. However, this positioning of the wheel 146, the cable 148, and the first motor 126 are not strictly necessary.

Referring again to FIGS. 1, 11-12, the rotating arm 124 is disposed on the mount 104 through a rotatable connection such that the rotating arm 124 may rotate around the first axis 114 while the mount 104 remains stationary. Rotation of the wheel 146 around the first axis 114 causes corresponding rotation of the rotating arm 124 around the first axis 114. Thus, the rotating arm 124 may be driven by the first motor 126 to rotate around the first axis 114, which in turn causes corresponding rotation of the simulator chamber 102 around the first axis 114 via the connection between the rotating arm 124 and the simulator chamber 102. The belt tensioner 120 is disposed on, and connected to, both the rotating arm 124 and the simulator chamber 102. Thus, when the rotating arm 124 rotates around the first axis 114, the belt tensioner 120 and the simulator chamber 102 also rotate around the first axis 114.

Referring now to FIGS. 1-2, the belt tensioner 102 includes a belt 136 that runs in a loop around an arm wheel 138, a chamber wheel 140, and a central wheel 142. The central wheel 142 is raised relative to the chamber wheel 140 and the arm wheel 138 so as to cause sufficient tension in the belt 136. The belt tensioner 120 further includes a pin 144 which runs through one of the side members 134 of the rotating arm 124 so as to securely connect the belt tensioner 120 to the simulator chamber 102 in a manner in which the simulator chamber 102 rotates with the pin 144. The pin 144 rotates with the chamber wheel 140, which is turned by the belt 136, which is driven by the action of the second motor 118 on the arm wheel 138. The second motor 118 drives rotation of the arm wheel 138, which drives movement of the belt 136 along the loop of the belt tensioner 120 over the central wheel 142 and around the chamber wheel 140. Movement of the belt 136 over the chamber wheel 140 causes rotation of the chamber wheel 140 around the second axis 116, which in turn causes rotation of the pin 144 around the second axis 116, which in turn causes rotation of the simulator chamber 102 around the second axis 116. Advantageously, this allows the simulator chamber 102 to rotate around the second axis 116, as the simulator chamber 102 is simultaneously rotating around the first axis 114. However, the rotation may be accomplished using a variety of methods and technologies.

Referring now to FIGS. 1-3, 15-20, in particular embodiments, the adjustable gravity simulator 100 has a mechanical loading device 200. The mechanical loading device 200 may be disposed within the simulator chamber 102 and is configured to apply a mechanical load to samples in the simulator chamber 102 and/or in culturing chambers 112. Non-limiting examples of the mechanical load include predefined mechanical strains and frequencies. Desirably, this can allow the samples to be subjected to a physiologically relevant mechanical load, which can be used to simulate forces the samples would experience in vivo, while the samples are also experiencing a microgravity or partial gravity simulation. In other words, the mechanical loading device 200 can facilitate simulating what the sample would experience in a real tissue environment. In certain embodiments, as shown in FIGS. 1-3 and FIGS. 15-20, the mechanical loading device 200 has a loading chamber 202 with a lid 210 that can enclose and seal the loading chamber 202. The loading chamber 202 is configured to house the samples and/or culturing chambers 112 having the samples. In certain embodiments, the loading chamber 202 is interchangeable and autoclavable. The mechanical loading device 200 may include a third motor 204 to apply the mechanical load to the samples in the loading chamber 202. Referring to FIG. 3 specifically, the third motor 204 is configured to move the samples along a third axis 206, or an axis parallel to the third axis 206, in a preselected pattern. This may be accomplished, for example, utilizing a corkscrew mechanism in the loading chamber 202. In particular embodiments, the third motor 204 may be configured to move the samples axially along the third axis 206 in a back-and-forth manner. In an alternative embodiment, the mechanical loading device can include a loading plate 208 (shown in FIG. 4) configured to receive and support the samples and/or culturing chambers 112 having the samples. Desirably, the loading plate 208 may accommodate a plurality of the samples and/or culturing chambers 112. It should be appreciated that the simulator chamber 102 and/or culturing chambers 112 and the mechanical loading device 200 may be provided separately from the adjustable gravity simulator 100 for culturing purposes unrelated to the adjustable gravity simulator 100. Furthermore, the adjustable gravity simulator 100 does not need to include the mechanical loading device 200, loading plate 208, or any other apparatus within the simulator chamber 102, and in some embodiments, the simulator chamber 102 is empty.

Referring now to FIGS. 1, 12, the adjustable gravity simulator 100 has a control module 128 in communication with the first motor 126, the second motor 118, and/or the third motor 204. The control module 128 includes a memory and a processor. The memory has a tangible, non-transitory computer readable medium with stored processor-executable instructions. The control module 128 is configured to control the microgravity or partial gravity simulation by controlling the directions and speeds of rotation of the simulator chamber 102 around the first axis 114 and the second axis 116. In particular, the control module 128 may be used to direct the rotation, a speed, and/or a direction of the rotating arm 124 relative to the mount 104, or movement of the belt 136, and/or the actuation of the mechanical loading device 200 along the third axis 206, via the first motor 126, second motor 118, and/or third motor 204. The control module 128 may control these variables based on an algorithm for achieving a desired level of gravity experienced by the simulator chamber 102. The control module 128 may include one or more ports 162 for receiving a connection from a computing device for inputting data or for making an output connecting such as to a monitor. The control module 128 may also be capable of wireless connections, such as Bluetooth® connections, with smart devices.

Referring still to FIG. 1, in certain embodiments, the control module 128 includes a touchscreen 130 with a graphical user interface. The graphical user interface is configured to accept inputted information relating to gravitational data, mechanical loading strain, and/or mechanical loading frequency. Other information may also be accepted by the graphical user interface, as desired. Desirably, the touchscreen 130 permits the user to conveniently control and program the adjustable gravity simulator 100, according to the goal of the current experiment.

Referring still to FIG. 1, the adjustable gravity simulator 100 has one or more sensors 132 to facilitate the creation and validation of a desired level of gravity (i.e., microgravity or partial gravity) simulation. Each of the sensors 132 is in communication with the control module 128 and is configured to collect the gravitational data through measurements. Non-limiting examples of the sensors 132 include gyroscopes, accelerometers, load cells, and force sensing resistors. In a particular embodiment, the sensors 132 include at least one accelerometer. The accelerometer can measure the proper acceleration to determine and validate that samples within the simulator chamber 102 are experiencing the desired microgravity or partial gravity simulation. It should be appreciated that one skilled in the art may employ additional sensors 132 to capture data points to aid in creating and validating the microgravity or partial gravity simulation, and such additional sensors are within the scope of the present disclosure.

Figure 9:
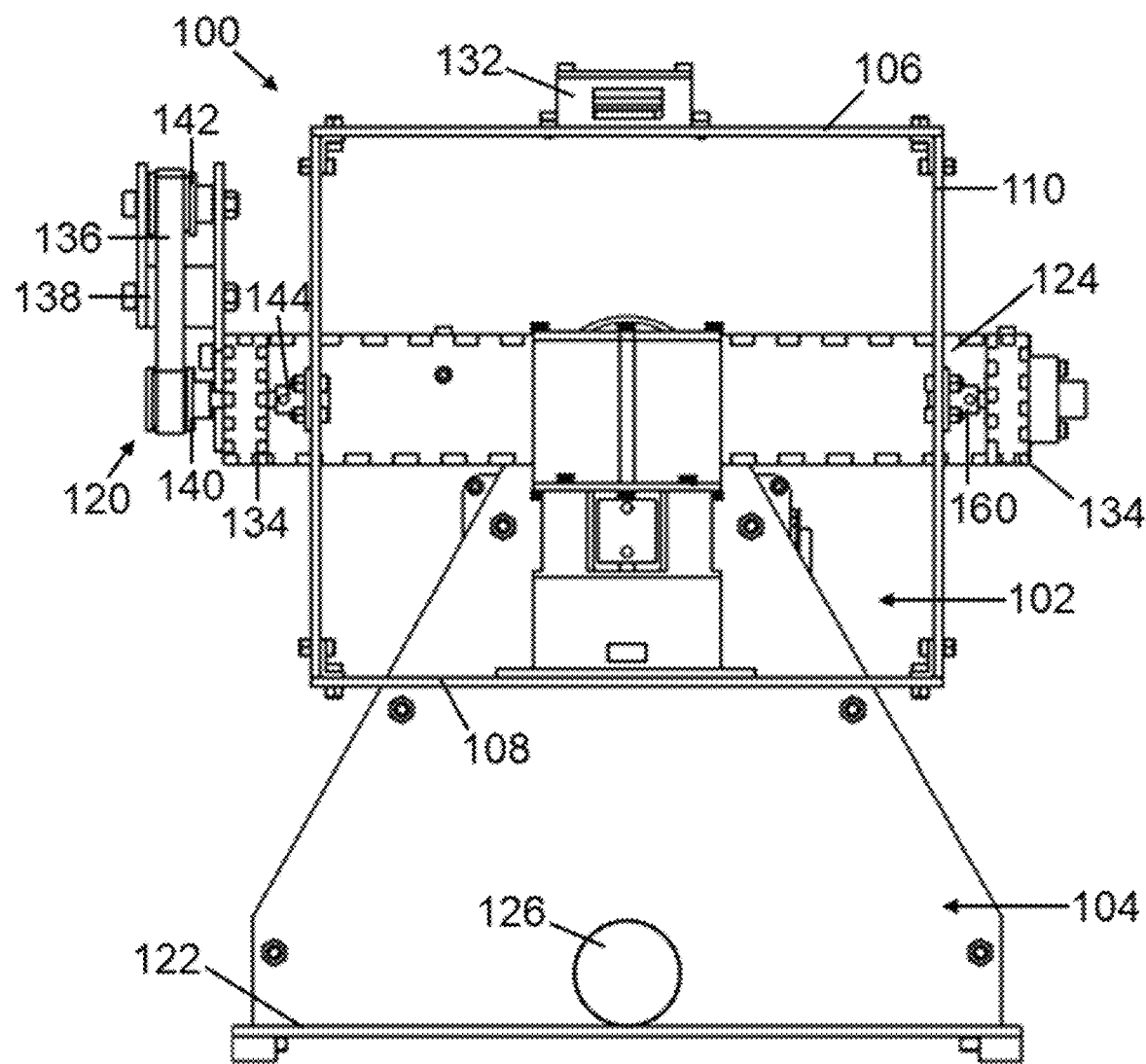
FIG. 9: Front elevational view of an adjustable gravity simulator, according to one embodiment.
Figure 10:
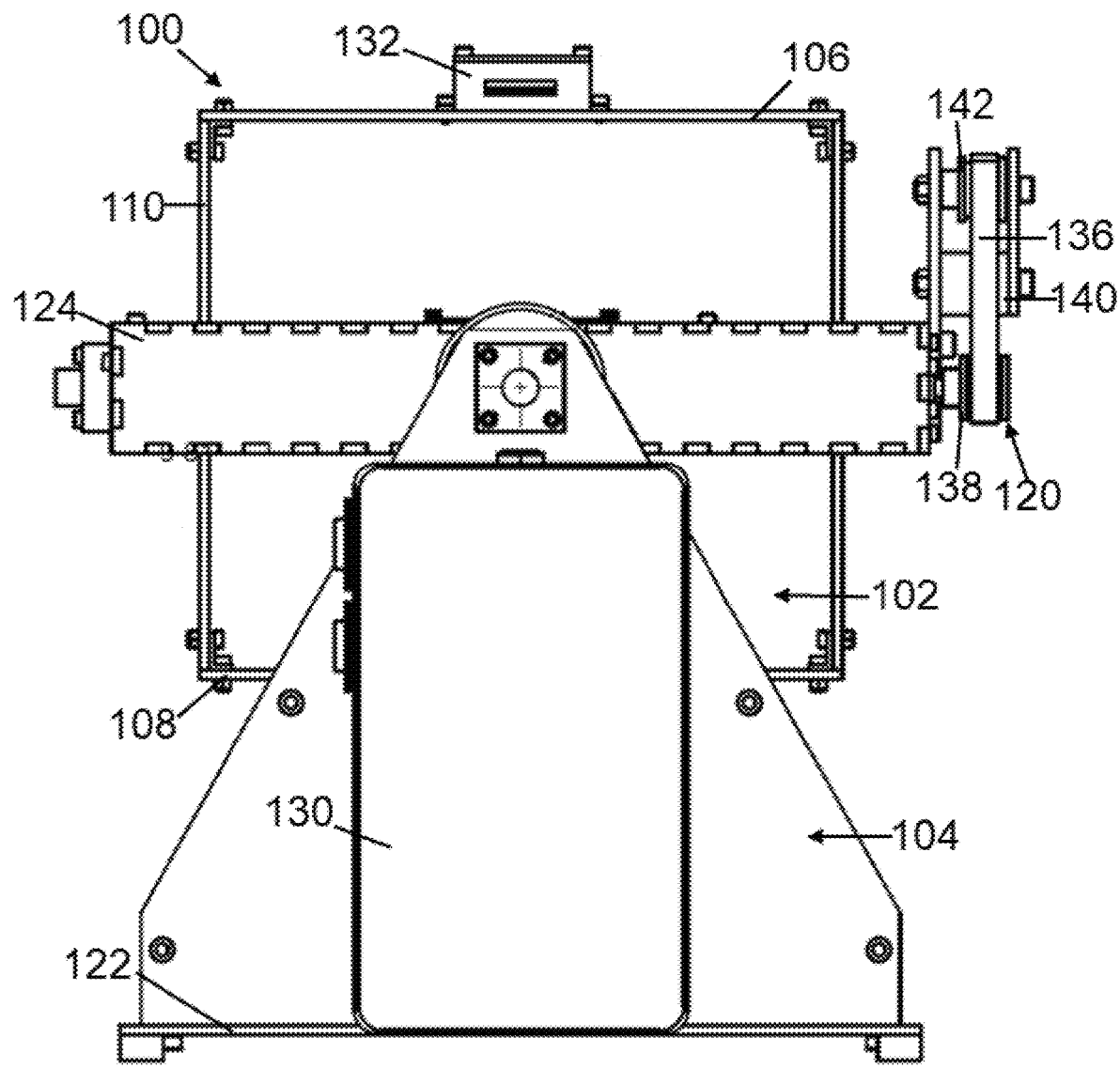
FIG. 10: Rear elevational view of the adjustable gravity simulator shown in FIG. 9.
Figure 13:
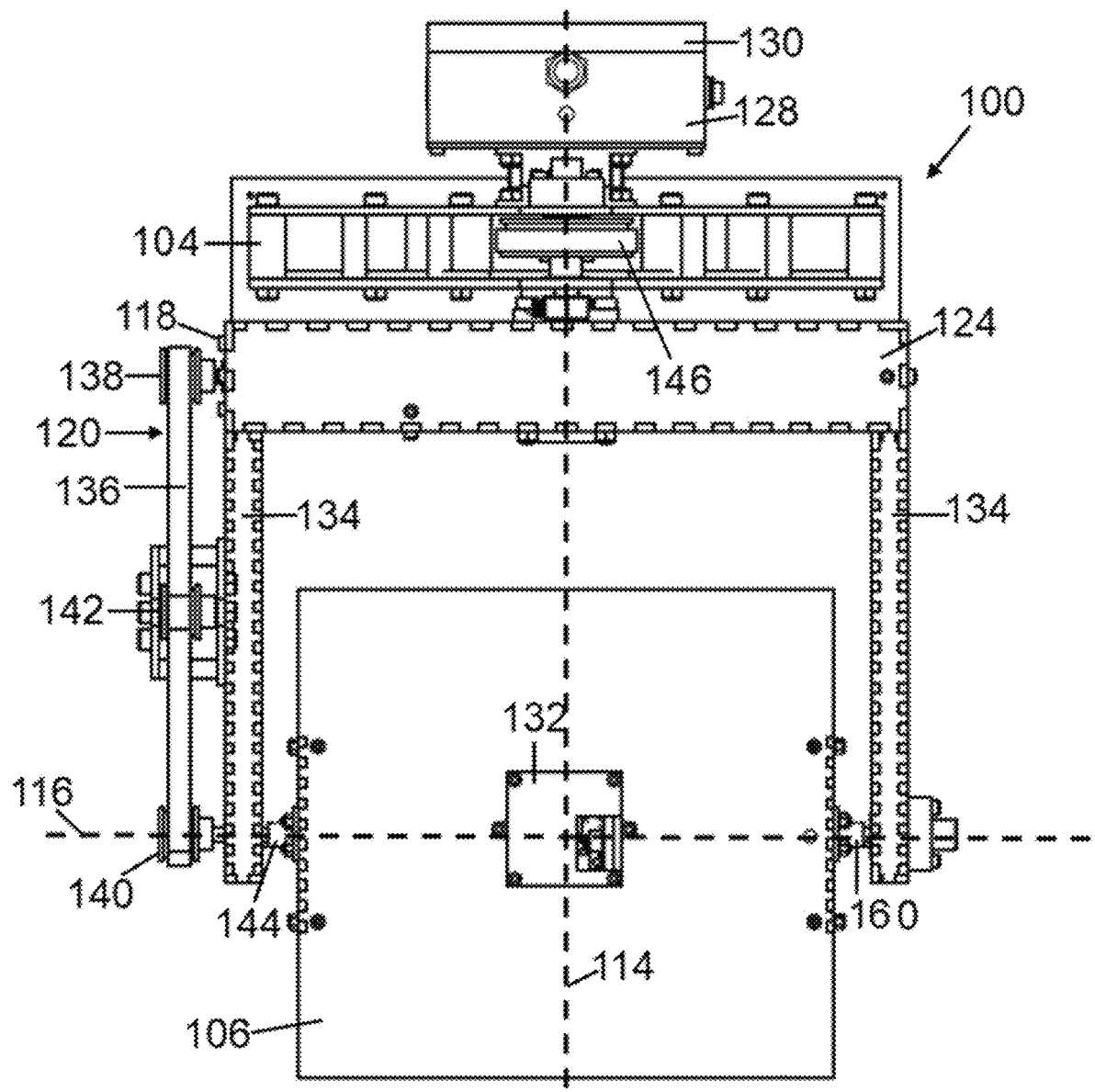
FIG. 13: Top plan view of the adjustable gravity simulator shown in FIG. 9.
Figure 14:
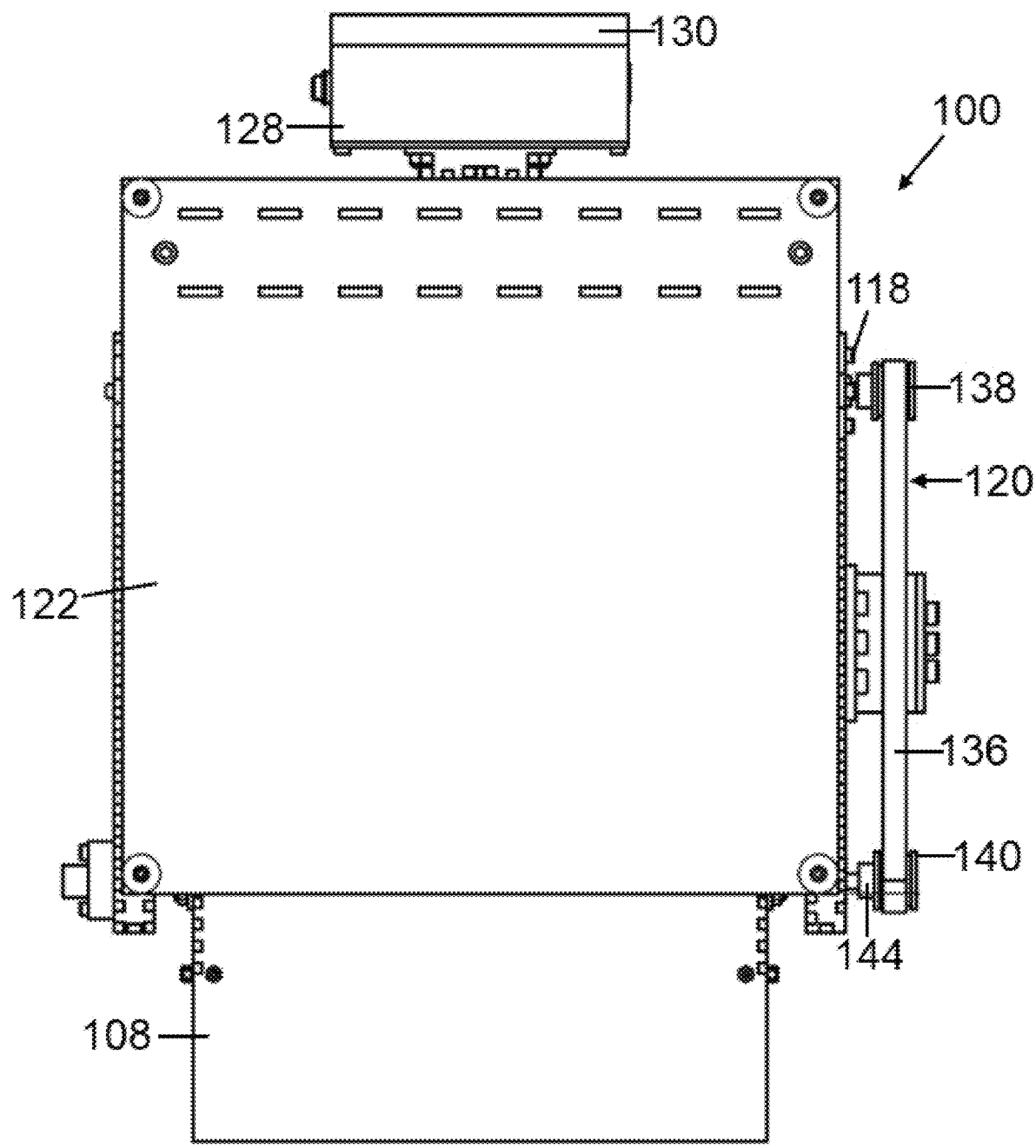
FIG. 14: Bottom plan view of the adjustable gravity simulator shown in FIG. 9.
Figure 15:
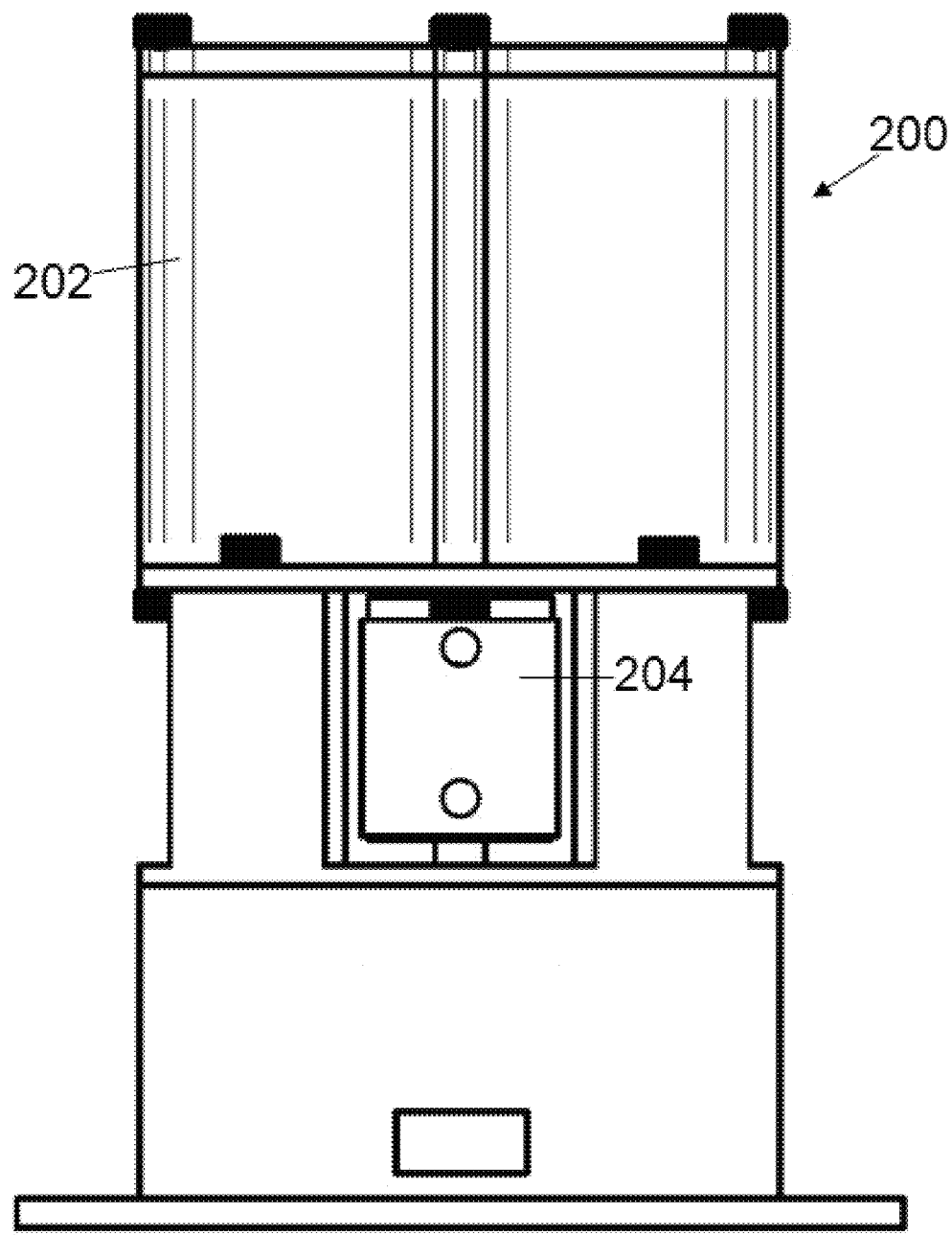
FIG. 15: Front elevational view of the mechanical loading device, according to one embodiment.
Figure 16:
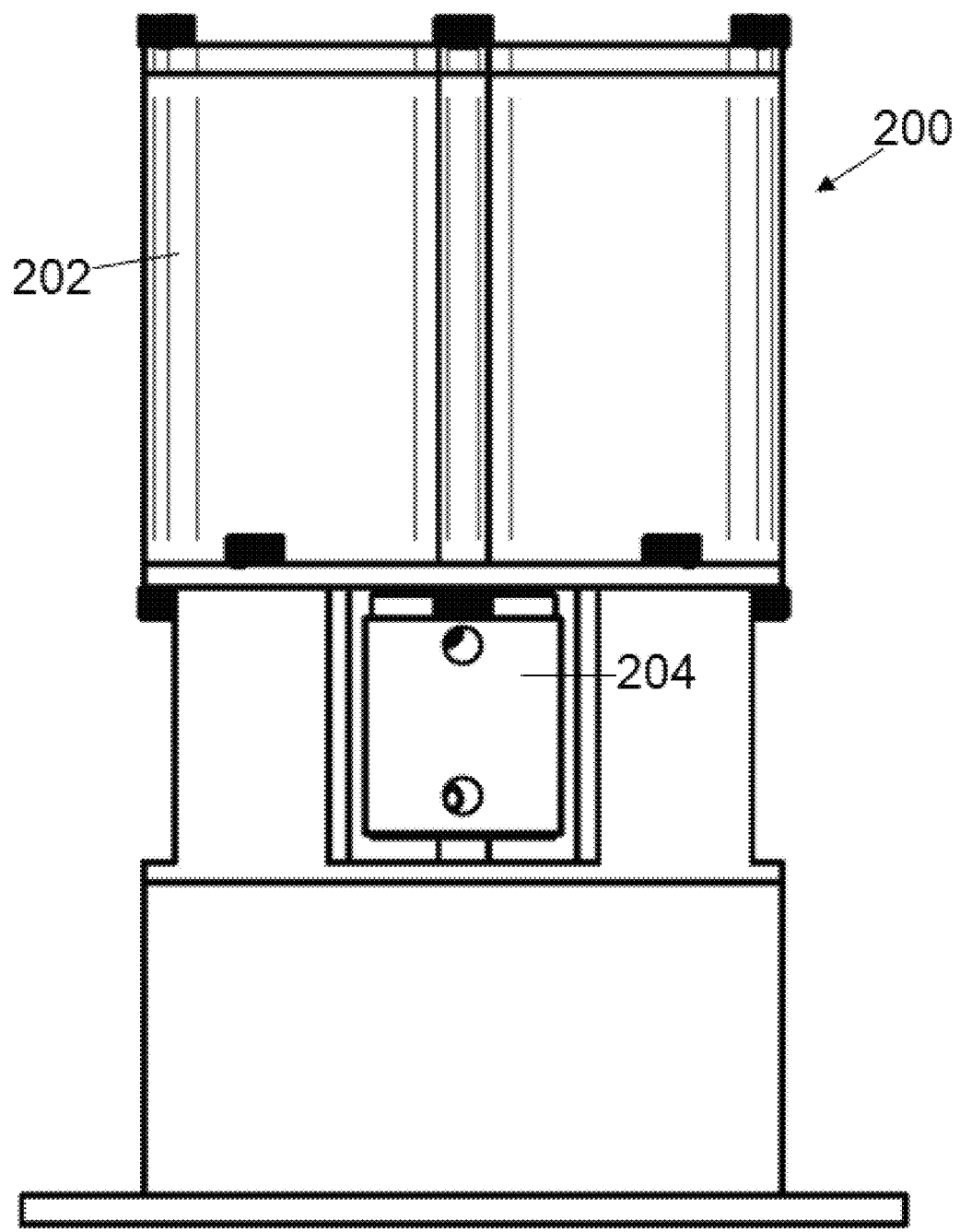
FIG. 16: Rear elevational view of the mechanical loading device shown in FIG. 15.
Figure 17:
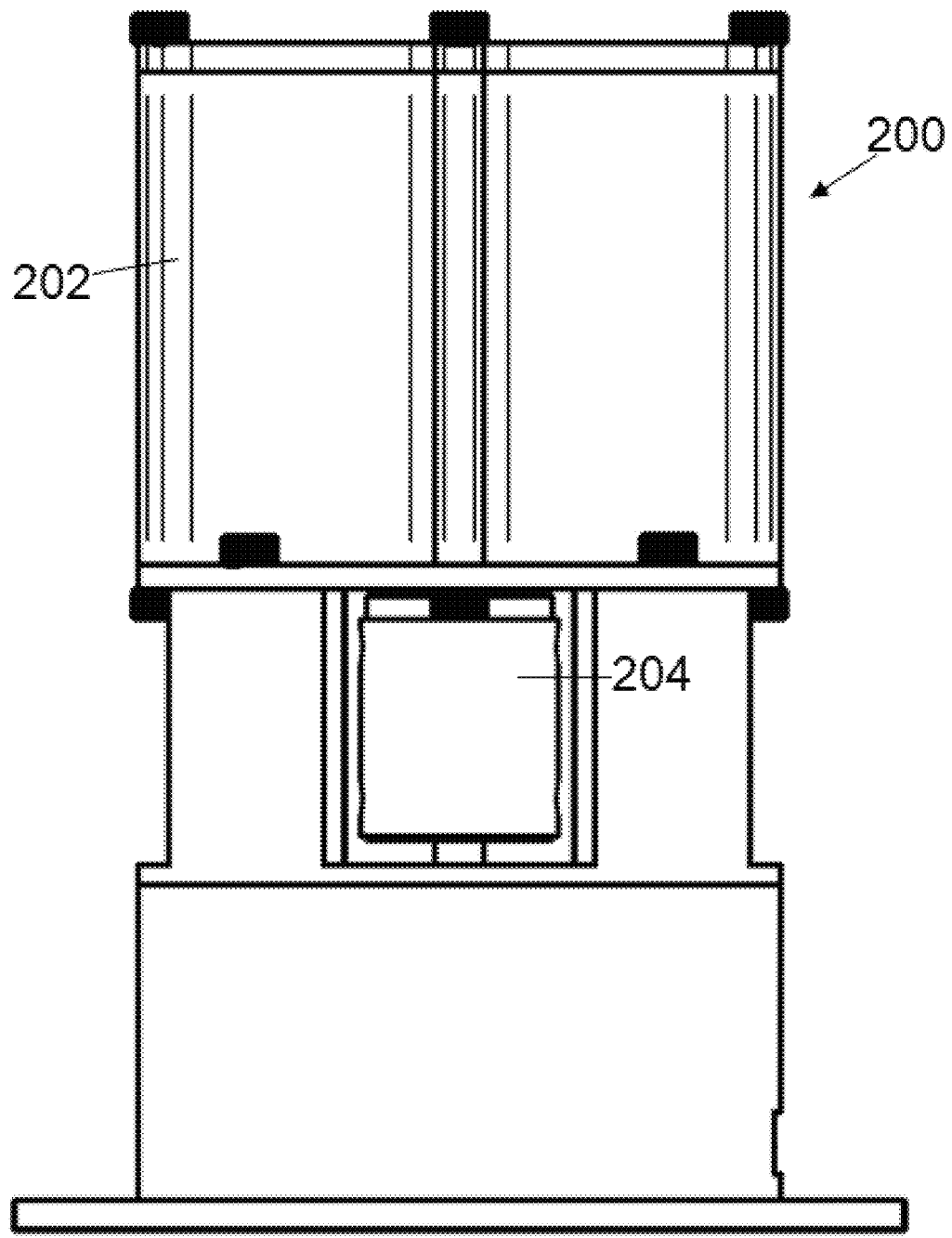
FIG. 17: Left elevational view of the mechanical loading device shown in FIG. 15.
Figure 18:
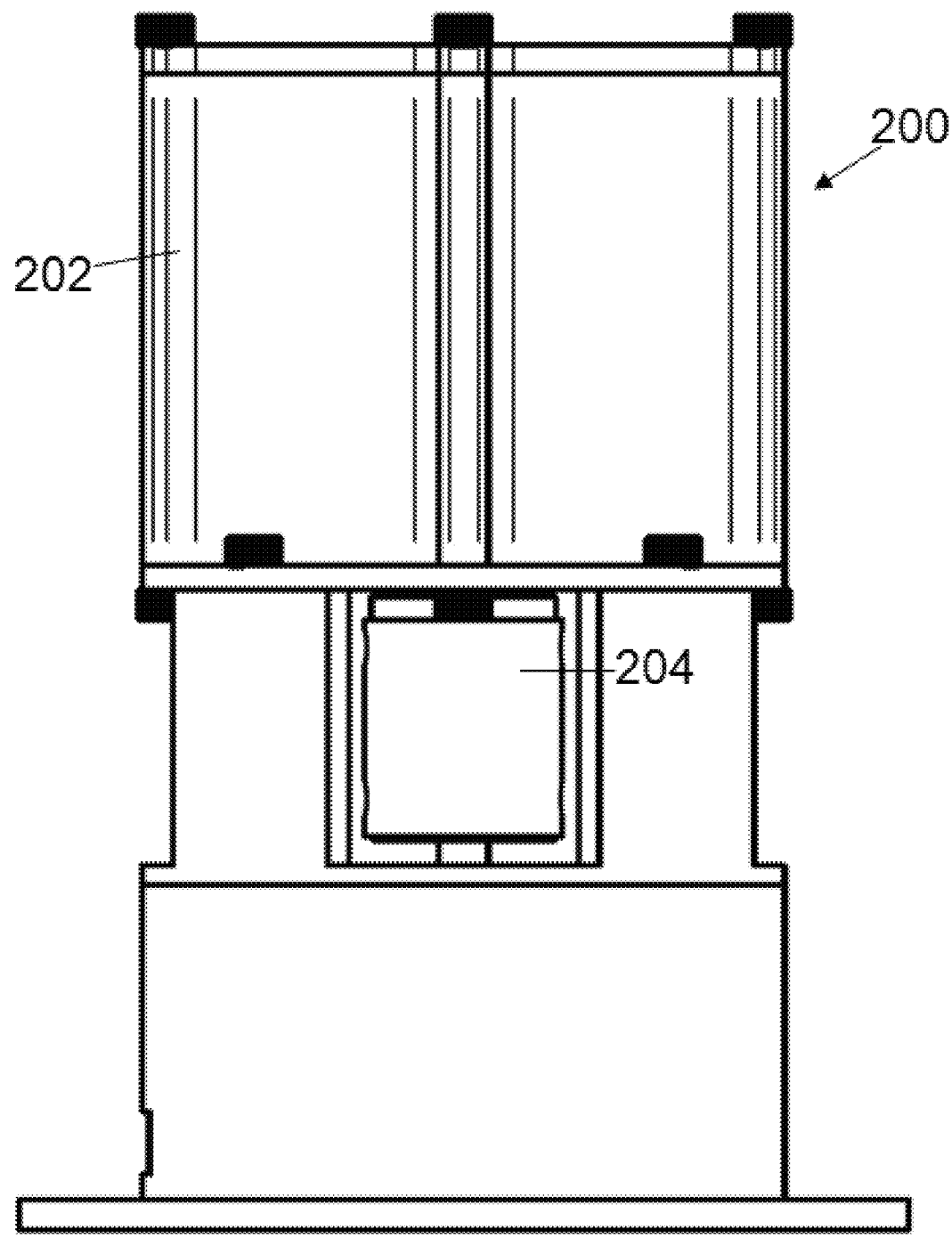
FIG. 18: Right elevational view of the mechanical loading device shown in FIG. 15.
Figure 19:
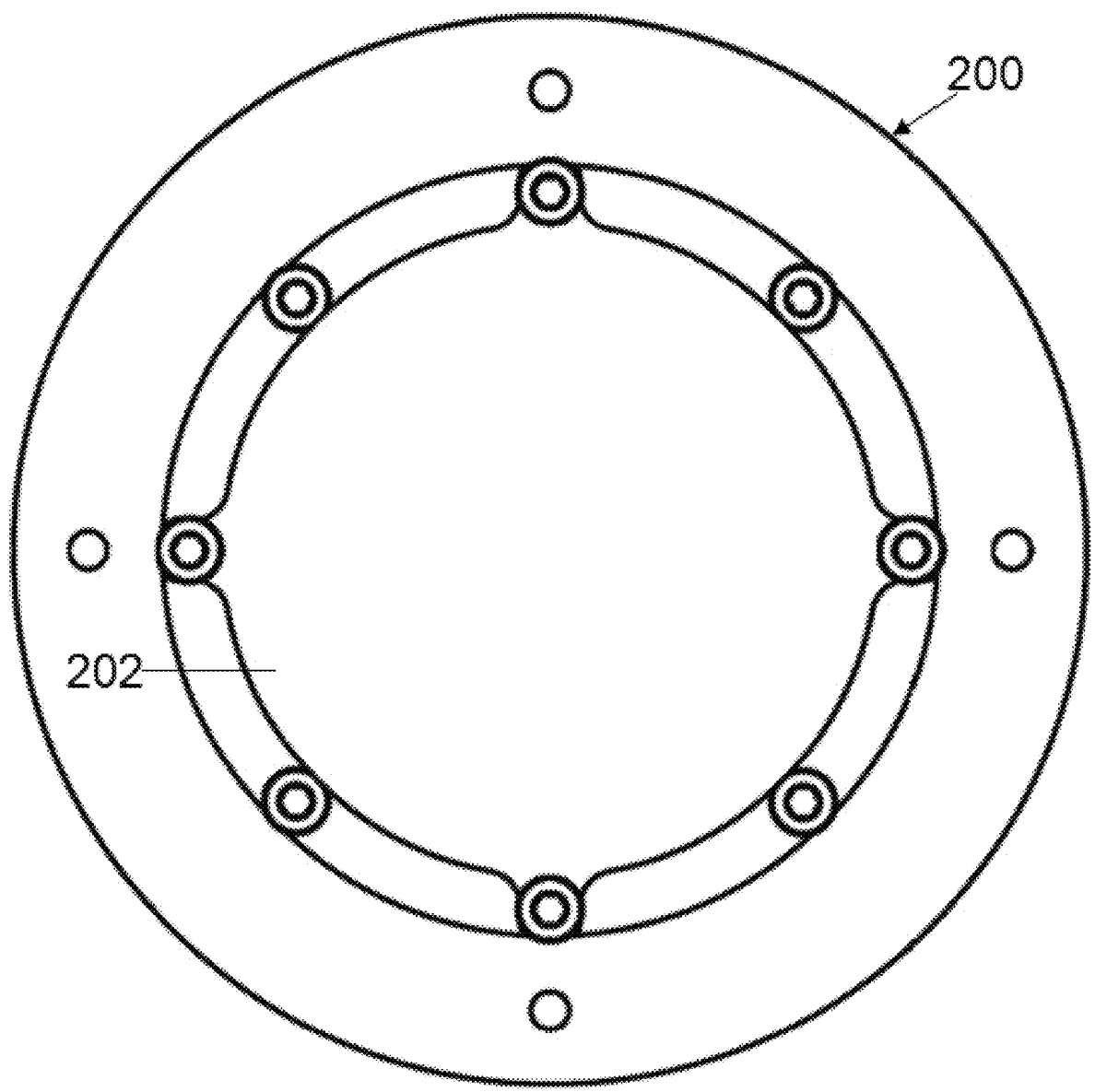
FIG. 19: Top plan view of the mechanical loading device shown in FIG. 15.
Figure 20:
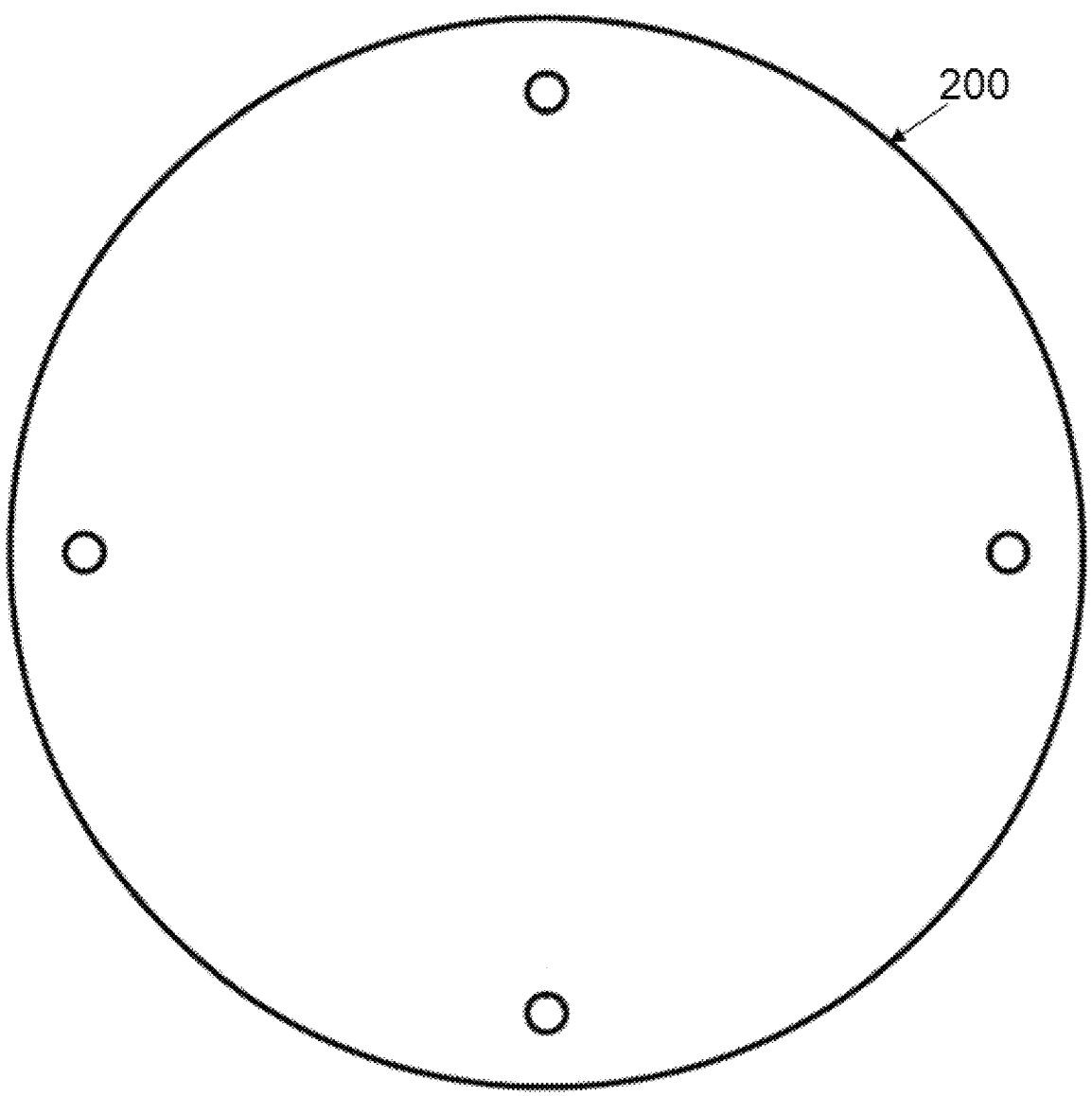
FIG. 20: Bottom plan view of the mechanical loading device shown in FIG. 15.

Referring now to FIGS. 9, 12-13, the adjustable gravity simulator 100 includes one or more slip rings 160, such as at the connection between the mount 104 and the rotating arm 124 and the connection between one or both of the side members 134 and the simulator chamber 102. The slip rings 160 can be configured to provide electricity to the simulator chamber 102 and/or the culturing chamber within the simulator chamber 102. Specifically, the slip rings 160 allow the transmission of power and electrical signals from an external source to the rotating structures, such as the rotating arm 124 and/or the simulator chamber 102. Advantageously, this provides electricity to the mechanical loading device 200, when present, while allowing the simulator chamber 102 to rotate. However, it should be appreciated that a skilled artisan may employ the slip rings 160 for other functions such as providing electricity to the samples and/or other components found in the testing chamber and/or culturing chamber. In addition, it should be further appreciated that one skilled in the art may select different methods and technologies for providing electricity to the simulator chamber 102 and/or the culturing chamber. For example, electromagnetic power transmission methods are possible and encompassed within the scope of the present disclosure.

A method of simulating gravitational loads may include rotating the simulator chamber 102 around the first axis 114 and independently rotating the simulator chamber 102 around the second axis 116, where the rotation of the simulator chamber 102 around the first axis 114 may be at a different speed than the rotation of the simulator chamber 102 around the second axis 116. The simulator chamber 102 may be rotated around the first axis 114 in a first orientation (i.e., direction, such as clockwise or counterclockwise) and at a first speed and may be rotated around the second axis 116 in a second orientation at a second speed until a desired average g-force is experienced by the simulator chamber 102. Optionally, the first orientation and the second orientation may be changed one or more times to achieve the desired average g-force experienced by the simulator chamber 102, and may be changed independently and at random intervals according to an algorithm seeking to obtain the desired average g-force. Similarly, the first speed and the second speed may be changed one or more times to achieve the desired average g-force experienced by the simulator chamber 102, and may be changed independently and at random intervals according to an algorithm to obtain the desired average g-force.

In one example, to simulate microgravity, the first orientation and the second orientation may be inverted at random intervals to create a unique path that substantially facilitates no particular orientation being visited more than others. The first speed and the second speed may be constant while simulating microgravity. In addition, the speeds may be randomly changed to facilitate creating the unique path. Simulating microgravity can be particularly beneficial when samples need to experience environments similar to the International Space Station (ISS). "Biasing" refers to the simulator chamber 102 spending more time soaking the experiment with Earth gravity, while still canceling a certain percentage of it. When the adjustable gravity simulator 100 is operating in pure microgravity mode, no biasing occurs because all orientations must be soaked with an equal amount of Earth gravity. Therefore, the simulator chamber 102 rotates randomly when generating microgravity. In another example, to simulate partial gravity, the first speed or the second speed is biased so that at least one orientation is visited more than others. When generating partial gravity, biasing the rotation means adjusting the rotational velocity to cause the upward facing orientation of the experiment chamber to experience the Earth's force due to gravity longer than all other orientations. Desirably, the biasing can be adjusted to simulate environments that have partial gravity relative to Earth, such as the Moon or Mars. It should be appreciated that a skilled artisan may employ different configurations to simulate microgravity or partial gravity, within the scope of this disclosure. Further details regarding the structure and operation of the adjustable gravity simulator 100 are described in the examples below.

Many current challenges faced in the simulated microgravity cell culturing process can be addressed and overcome with the present disclosure. First, the adjustable gravity simulator can provide three-dimensionality in culturing like in real-life examples. In simulated microgravity or microgravity environment, the cell cultures are primarily conducted on 2D surfaces including petri dishes, well plates, and cell culture flasks, which only provide monolayer expansion of the cells. The spheroids with cell aggregates achieve by rotating wall vessel culturing can only reach up to 800 μm diameter, which does not sufficiently represent the three-dimensionality and structural features of the tissue. The present disclosure provides a platform where cell-laden 3D tissue constructs prepared by various natural and synthetic biominerals can be cultured for significant amounts of time, such as more than three months.

Second, the adjustable gravity simulator can apply mechanical stimuli to the tissue and organ. In conventional simulated microgravity or microgravity environments, without exception, the cell culture is done under static cell culturing conditions without considering the mechanical loading that the tissue is exposed to including compression, tensile, and biaxial mechanical loading. Conventional microgravity simulation platforms are not designed to apply physiologically relevant mechanical strain and frequency to the cells cultured under a simulated microgravity environment. In contrast, the adjustable gravity simulator described herein can apply physiologically relevant mechanical loading to the construct (3D tissue or organ) using a computer-controlled mechanical loading platform.

Third, the adjustable gravity simulator can culture musculoskeletal organs. Musculoskeletal organs are affected most in a microgravity environment. However, no commercially available clinostats can offer culturing of musculoskeletal organs in a simulated microgravity environment. In some embodiments, the adjustable gravity simulator described herein has an interchangeable culturing chamber that can be changed to a bigger size to accommodate organs including intervertebral disc (IVD), tendon, bone, cartilage, and muscle. The organs can be cultured under a pre-defined simulated microgravity environment for an extended period of time, such as a month, to study the effects of microgravity on tissue and cells within the important musculoskeletal organs.

Fourth, the adjustable gravity simulator can monitor and validate a pre-defined gravity environment is advantageous. Validating the pre-defined microgravity that samples experience is key in a microgravity study. Conventional technologies do not sufficiently validate results. The adjustable gravity simulator of the present disclosure can monitor gravitational forces using an accelerometer unit and record this data to validate that experiment samples experienced microgravity.

Fifth, the adjustable gravity simulator can reach a desired partial gravity. Microgravity can be achieved by rotating each axis at a constant speed, while randomly changing the direction. The randomness guarantees that no particular orientation is visited more than others. Generating a partial gravity environment involves biasing the rotational speeds so that samples are exposed to the parent gravitational vector for a longer period. No conventional clinostats can guarantee that partial gravity will be reached without pre-planning their trajectory. This introduces determinism and creates the ability for extraneous forces to be introduced. In contrast, the adjustable gravity simulator described herein utilizes an accelerometer unit, along with a feedback-based approach that visits all orientations and ensures that some are biased more than others. This also allows the adjustable gravity simulator to reach its target partial gravity within an average of 60 to 90 seconds after initiation.

Sixth, the adjustable gravity simulator can include useful interfacing and control. Conventional partial-gravity simulation platforms require a connection to an external computer to provide the device with instructions on how to reach the target gravity. Existing platforms also provide no feedback as to whether they have reached their target gravity yet. In some embodiments, the adjustable gravity simulator described herein utilizes a touchscreen and motor controllers to instruct the device on what partial gravity to generate and provide visual feedback on its gravitational status.

Seventh, the adjustable gravity simulator makes powered experiments possible. Due to the difficulty of passing wires through rotational axes, existing clinostat platforms do not provide adequate electrical connections for experiments that require motors or additional sensors within the micro/partial gravity environment. As a result, usage of a computer-controlled mechanical loading platform is not possible with existing clinostats. The adjustable gravity simulator of the present disclosure may include multiple slip rings that provide 8 connections for experiments to pass signals and power through the rotational axes. Additionally, up to 240V at 2 A can be passed into the micro/partial gravity environment. These connections also allow for additional sensors to send live data back while the device is actively generating micro/partial gravity.

Additional advantages of the present disclosure include the ability to culture single or multiple cells from different tissues within a 3D tissue-like matrix; the ability to accommodate various in vitro tissue volumes, cell type, cell density, and biomaterial selection without any restriction; the ability to operate at a wide range of loading strains and frequencies due to the high torque stepper motor driven by a user-friendly GUI (graphic user interface)-based programmable controller; the ability to apply different types of loading regimes, such as static and symmetric/asymmetric cyclic, with the possibility of inserting rest periods and ramping up strain and frequency with a duration of loading; the ability to mimic the broad range of the strain and frequency values to mimic any phase of human tissue, including physiological, acute, and chronic injuries, and healing and rehabilitation; the ability to create adjustable simulated microgravity environment (low Earth-orbit gravity, Martian gravity, lunar gravity) and partial gravity environment through altering the rotation speed of the axes; the ability to operate at the predefined microgravity within 60-90 seconds after initiating the device; the ability to monitor the gravitational force and validate the pre-defined gravity; the ability to culture tissues and organs of different sizes through the interchangeable culturing chamber; the ability to adjust the internal temperature and $CO_2$ level (for example 37° C. 5% $CO_2$) in the culturing chambers for benchtop studies; and being compact enough to place in an incubator for long-term cell culturing (over months) at 37° C. 5% $CO_2$.

EXAMPLES

These examples describe the development of a biomimetic engineered space technology platform usable as an adjustable gravity simulator.
Design and Principles The biomimetic engineered space technology platform (i.e., the adjustable gravity simulator) provides a physiologically relevant recapitulation of in vivo mechanism in a simulated extraterrestrial gravity (e.g., low-Earth orbit, Martian gravity, and lunar gravity) environment using 3D in vitro and organ culture models under physiologically relevant mechanical loading environment. As illustrated in FIG. 4, a biomimetic engineered space technology platform was made to include a microgravity simulator (1) that creates a frame to attach a mechanical loading device (2) and a culturing chamber (3). The culturing chambers (3) were individually designed containers to culture cell-laden tissue scaffolds, 3D tissues, or an organ such as an intervertebral disc. The size of the culturing chamber (3) was capable of being changed based on the samples to be cultured. The culturing chambers (3) were mounted to the mechanical loading device (2) which applies pre-defined mechanical strain and frequency to the samples by creating cyclic up-and-down movement driven by a stepper motor. An accelerometer (4) was mounted at the top of the biomimetic engineered space technology platform to function as a gravity sensor. The adjustable gravity simulator utilized the accelerometer (4), along with a feedback-based approach that visits all orientations and ensures that some are biased more than others. This also allows the adjustable gravity simulator to reach its target partial gravity within an average of 60 to 90 seconds after initiation. The accelerometer (4) also collects microgravity data for validation purposes. A belt tensioner (5), an outer axis motor (6), and an inner axis motor (7) help rotate the microgravity simulator axes to reach the pre-defined microgravity value. A touchscreen (8) functions as a user interface by which the user can input values of independent variables including microgravity, mechanical loading strain, and/or mechanical loading frequency. The accelerometer (4) can also communicate with the touchscreen (8) and send a signal when the pre-defined microgravity values are reached.

In the present examples, the parts of the mechanical loading device (2) were made up of polycarbonate, aluminum, or stainless steel. These materials were chosen with consideration of the environment in which the device would be under operation. Polycarbonate makes up the main framework of the device, including all of the supports. The material is light, sturdy, capable of bearing weight, biocompatible, and resistant to corrosion at high humidity and 37° C. (the typical culture temperature for cell-based studies). Aluminum was used for the pins and connecting rods due to its case of machining and anti-corrosion properties, while stainless steel was chosen for its robustness, durability, and anti-corrosion properties for parts under wear and tear that include the ball screw assembly and the coupling.

Figure 5:
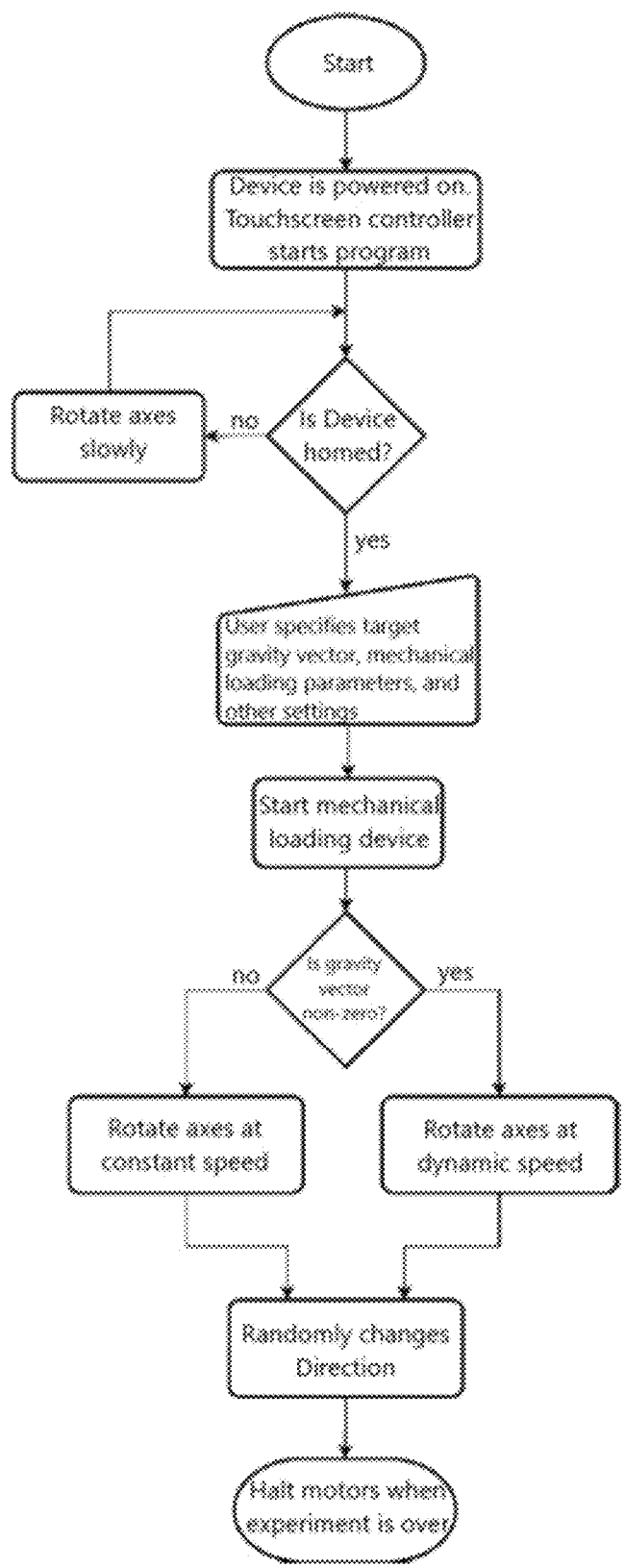
FIG. 5: Flowchart illustrating a non-limiting example of a workflow for the adjustable gravity simulator.

With reference to FIG. 4, the microgravity simulator (1) in these examples included two 20 cm by 20 cm plates separated by 18 cm vertical support-bars. Experiments were mounted to the plates and rotated along two axes that cut through the center. The inner axis of rotation was connected directly to the vertical support-bars via shafts and hubs on both sides. Rotational force was generated by a motor outside the microgravity simulator (1) and was transferred by the belt and pully to the shaft on one side. This force was then transferred through the mounting plates to the other shaft on the opposite side. The non-motorized shaft contained a slip ring that allows for wires to be passed into the microgravity simulator (1). A total of twelve wires were passed, however, two were used for signals to the accelerometer (4), and another four were used to drive the mechanical loading device (2). This left 6 additional wire hookups that could be utilized by other experiments. However, one skilled in the art can scale the number of wires, within the scope of this disclosure. The wires and slip rings can deliver high currents and are suitable to drive multiple independent motors inside the microgravity simulator (1). The accelerometer (4) was secured to the backside of the upper mounting plate. This accelerometer (4) was used to validate the device, provide live data, and generate partial gravity. The microgravity simulator (1) can support loads of up to 15 kg and various geometries. It should be appreciated that the microgravity simulator (1) can be scaled to accommodate different loads and geometries, as desired.
Operation of the Microgravity Simulator FIG. 5 shows an overview of an operation of the biomimetic engineered space technology platform in these examples. The microgravity simulator was operated via a software program being displayed on the touchscreen-controller mounted on the biomimetic engineered space technology platform. This program first provides an option to home the machine to the vertical position displayed in FIG. 4 to conveniently load experiments. Once homed, the program allows for the desired target gravity to be set on the scale of from zero to one-time earth's gravity via an input displayed on the screen. After this, controls are unlocked to start the mechanical loading device and begin the gravity simulation. As the gravity simulation progresses, the touchscreen-controller displays the average 3D acceleration vector being experienced by the experiment. This acceleration vector is measured by the accelerometer mounted within the microgravity environment and communicates its readings to the touchscreen-controller via a wired serial connection. An additional indicator is displayed by the program on the display once the target gravity has been achieved. During the gravity simulation, the touchscreen-controller periodically saves the average acceleration vector to a file for later analysis. This data can be used to validate those experiments achieved the target gravity simulation. The mechanical loading strain and frequency can also be configured via the touchscreen. The touchscreen controller is capable of running the experiment for both a pre-determined time, as well as with a manual start/pause button.

To create a microgravity environment, the biomimetic engineered space technology platform uses two independently rotating axes that are controlled by the program running on the touchscreen-controller. When the target gravity is zero, the axes are rotated at a constant speed. Their direction is inverted at random intervals to create a unique path that guarantees that no particular orientation is visited more than others. This ensures that no extraneous forces are generated, and the gravitational force of the parent body is completely mitigated. Generating a partial gravity environment involves biasing the rotational speeds so that the experiment is aligned with the parent body's gravitation vector for a longer period. The accelerometer is used as proportional feedback that determines the operation speed of the motors. This allows the target gravity to be reached within the first 60-90 seconds of operation. The motors operate at a maximum speed of 10 revolutions per minute and drive each axis by the belt and pulley. Each motor is rated with 15 kg·cm of torque and operates at a maximum of 0.6 amps at 12V DC. The speed and direction of the motors are controlled by an H-bridge circuit that is connected to the touchscreen-controller by pulse-width modulation. The biomimetic engineered space technology platform is capable of continuous operation with experiments that weigh up to 15 kg. Slip rings were used to pass wires through each axis and provide up to 8 connections for use with experiments. These slip rings are rated for 2 A at 240V on each wire and can drive multiple independent motors inside the microgravity environment.

Operation of the Mechanical Loading Platform

After defining the strain and frequency to be used in the studies, the samples within the loading chambers were cultured under the pre-defined mechanical loading conditions. Depending on the purpose of the study, the samples can be cell-laden tissue scaffolds, ex vivo tissue, or ex vivo organ. The present disclosure offers different sizes of chambers to be used in the platform. Once the samples were placed inside the chamber, the chamber was filled with the proper cell culture media and necessary reagents. The cell culture media was replaced every day based on experimental protocol. The lid of the chamber was tightly closed, and the mechanical loading was initiated using the user-interface touchscreen. The specific strain and frequency of the device can be set using the touchscreen program.

In a mechanical loading device, the high torque stepper motor, and its corresponding driver and controller give a wide range of operation in terms of strain and frequency values. The stepper motor with 200 steps per revolution (1.8° per step) ensures smooth operation and high precision. LabVIEW-based programming software is used to give command inputs to the controller which in turn drives the stepper motor to rotate at the desired number of revolutions and frequency, along with reversing the direction of motion to make it cyclic. The motor shaft transmits its rotation to the coupling system attached to the bottom of the culturing chamber, which causes the lower bottom of the chamber to move up and down in linear motion against the fixed chamber lid.

Operational Characterization-Creating Microgravity

Figure 6:
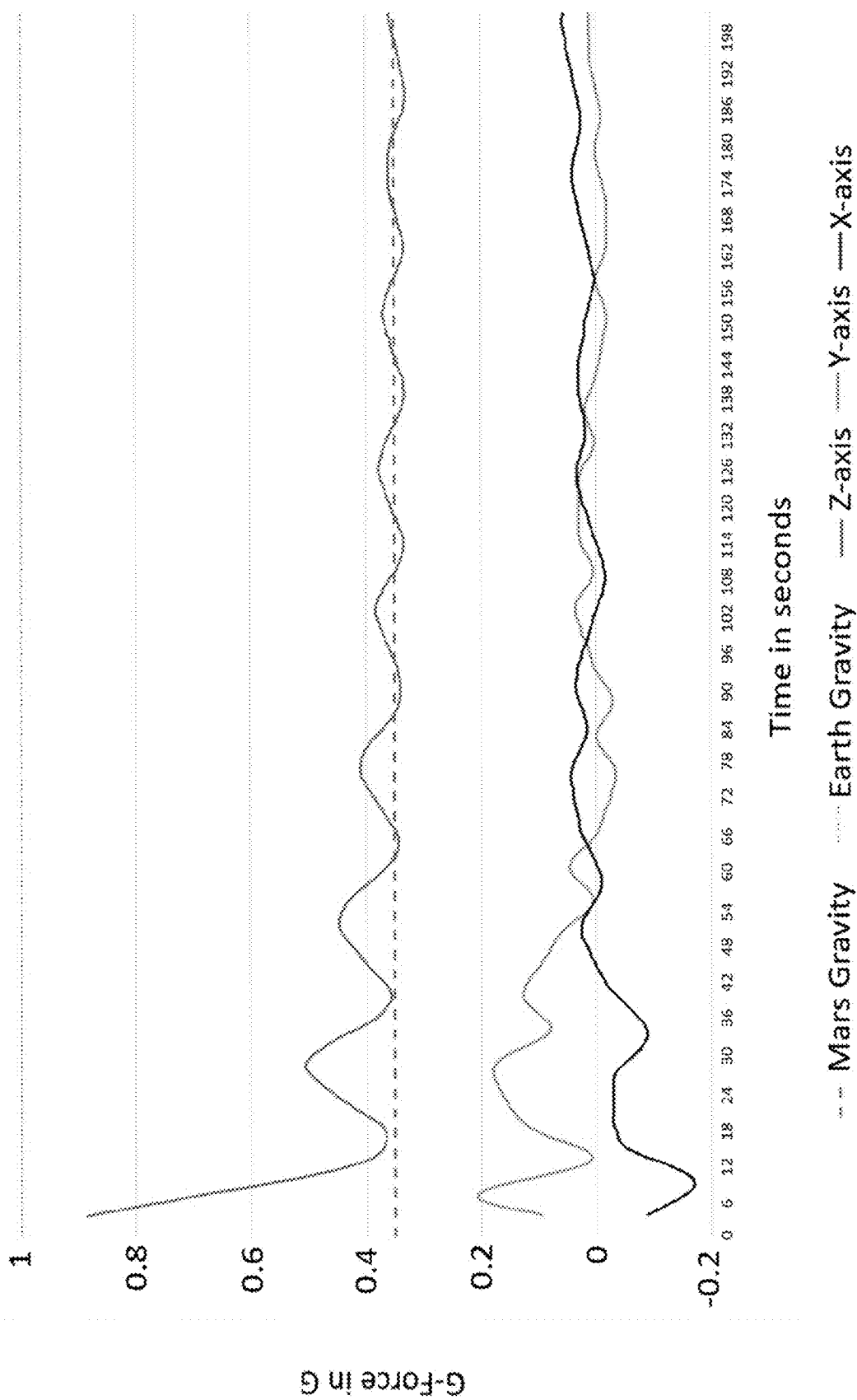
FIG. 6: Validation graph showing that the adjustable gravity simulator is capable of converging to a target 3D gravity vector. Specifically, the graph shows the adjustable gravity simulator simulating Martian gravity or 0.376 g.

Micro- and partial gravity were generated and validated with the integrated accelerometer on the device. Prior to device initiation a specific target gravity vector, $\vec{G}_{Target}=a_x\hat{i}+a_y\hat{j}+a_z\hat{k}$, can be specified on a scale of 0 to 1 times Earth's gravity for each component. This vector represents the average force due to gravity experienced by an experiment mounted within the simulator.

$$\vec{G}\,Avg = \vec{a}\,Avg = \frac{\sum \vec{a}\,n}{N}, \qquad \text{Equation 1,}$$

can be used to calculate the average gravitational vector from discrete samples of the acceleration vector. The average gravity vector is generated by the device, where N is the total number of discrete samples. Acceleration vector averaging can be used to validate the device's gravity simulation capabilities. For the example shown in FIG. 6, the system was configured with the target gravity vector of $\vec{G}_{Target}=0.0\hat{i}+0.0\hat{j}+0.376\hat{k}$ to match the 0.376 g of Martian gravity. Gravity simulation was then started. The acceleration vector was sampled, averaged, and recorded at a rate of 10 Hz according to Equation 1. The average is shown in FIG. 6 as a function of time on the interval 0 to 200 seconds. This graph shows how each component of the target vector converged to its specified value by 90 seconds. The X- and Y-components of the gravity vector converged to zero, while the Z-component converged to the 0.376 g Martian gravity.

Biological Characterization

The mechanical loading platform and its biological capacity have been validated through studying different cell lines within different biomaterials under various mechanical loading conditions. The following includes a listing of tested components. Cell Lines: Adipose-derived stem cells, pre-osteoblast cells, monocyte-derived macrophages. Loading Conditions: Mechanical strain (0%-15%) and frequency (0 Hz-5 Hz). Biomaterials: collagen, alginate, collagen-synthetic material composites.

Cell Viability and Structural Changes

Figure 7:
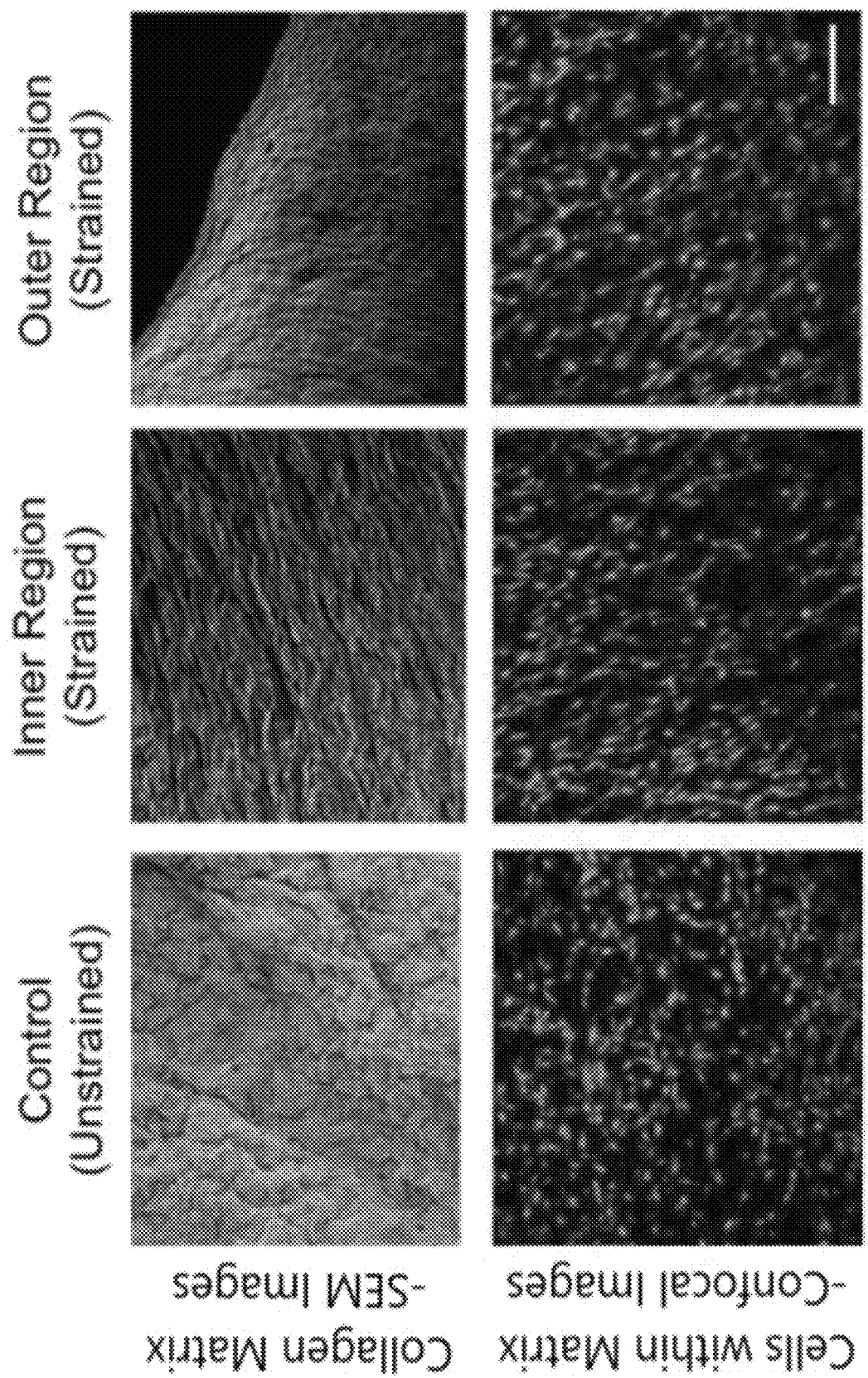
FIG. 7: Scanning electron microscopy (SEM) images showing collagen fibers (top row) and residing cells within the collagen matrices were visualized by confocal microscopy (bottom row). The cells were labeled with calcein-AM to illustrate live cells. Scale bar=100 μm.
Figure 8A:
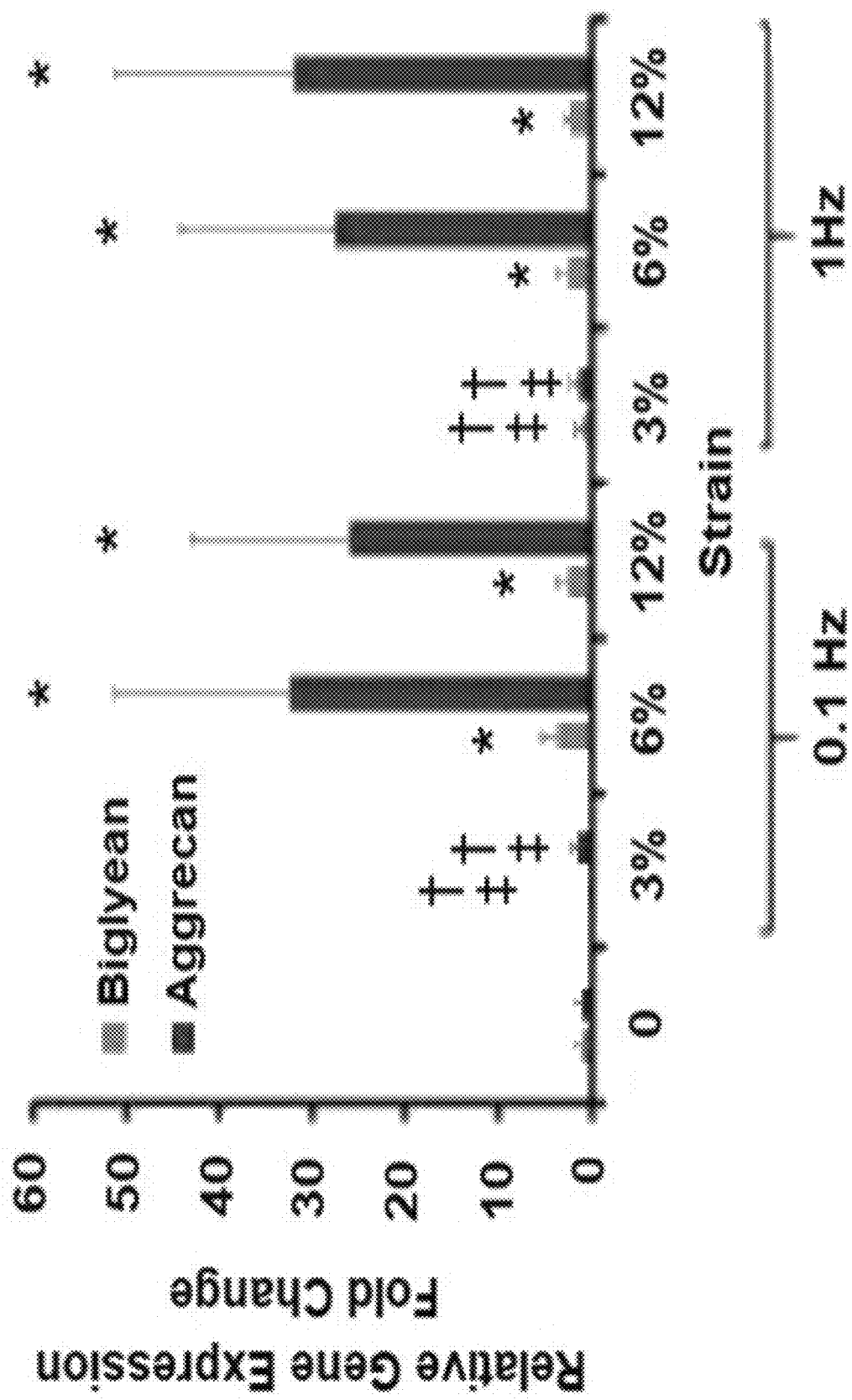
FIGS. 8A-8E: Graphs showing effect of varying magnitudes and frequencies of equiaxial strain on the gene expression profiles of the ECM proteins and different tissue markers. The gene expression profiles for the ECM proteins as well as AF markers were upregulated by equiaxial mechanical loading. Data represent the mean fold change (n=8), and the error bars represent the standard deviation. *Indicated significant difference concerning 0% strain group (control) with p<0.05. 5. § Represented significant difference between 0.1 Hz and 1 Hz (at the same strain magnitude), † Represented significant difference between 3% and 6% strain groups (at the same frequency), ‡ represented the significant difference between 3% and 12% strain groups (at the same frequency) while #represented the significant difference between 6% and 12% strain groups (at the same frequency), each with p<0.05.
Figure 8B:
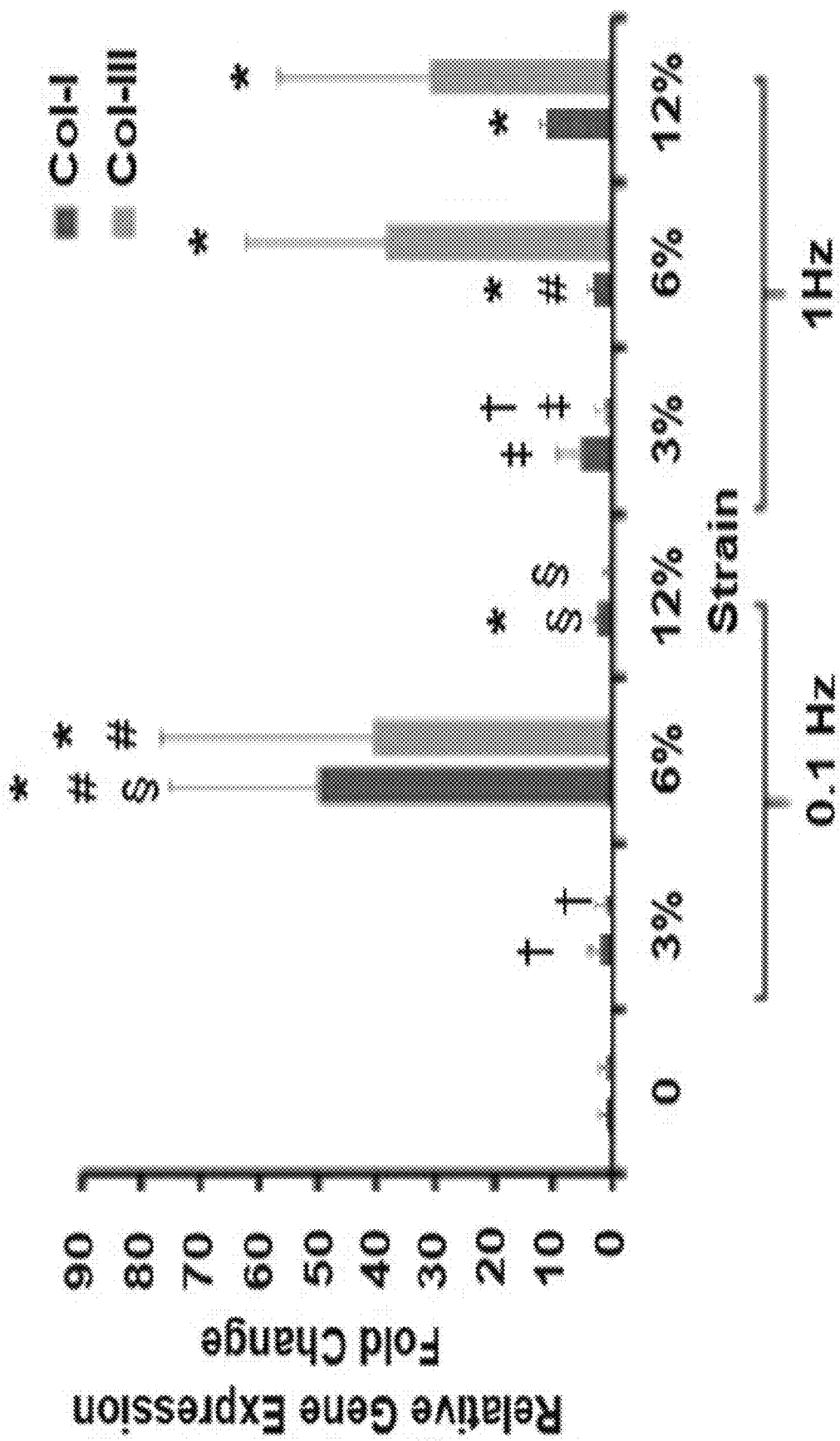
Figure 8C:
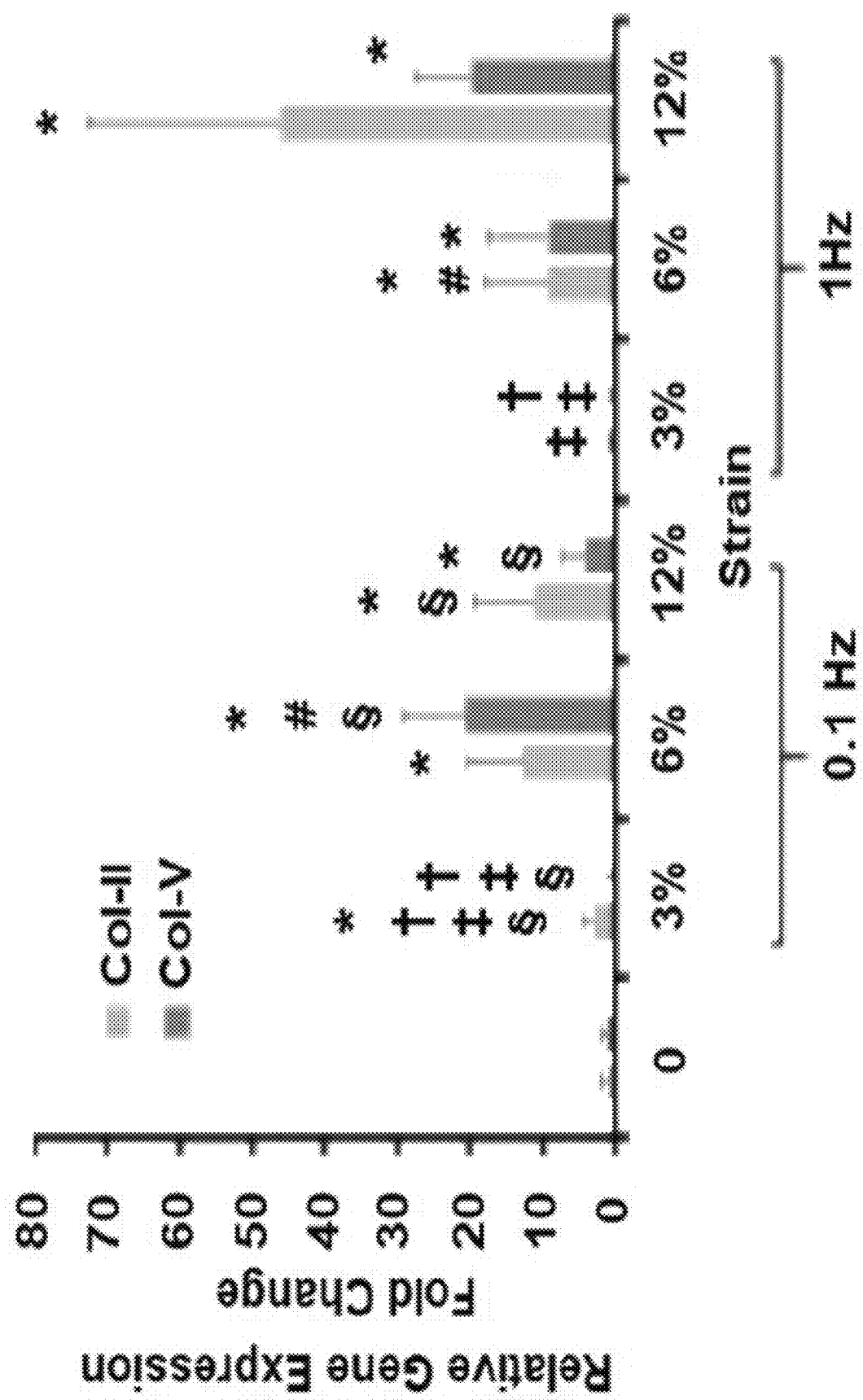
Figure 8D:
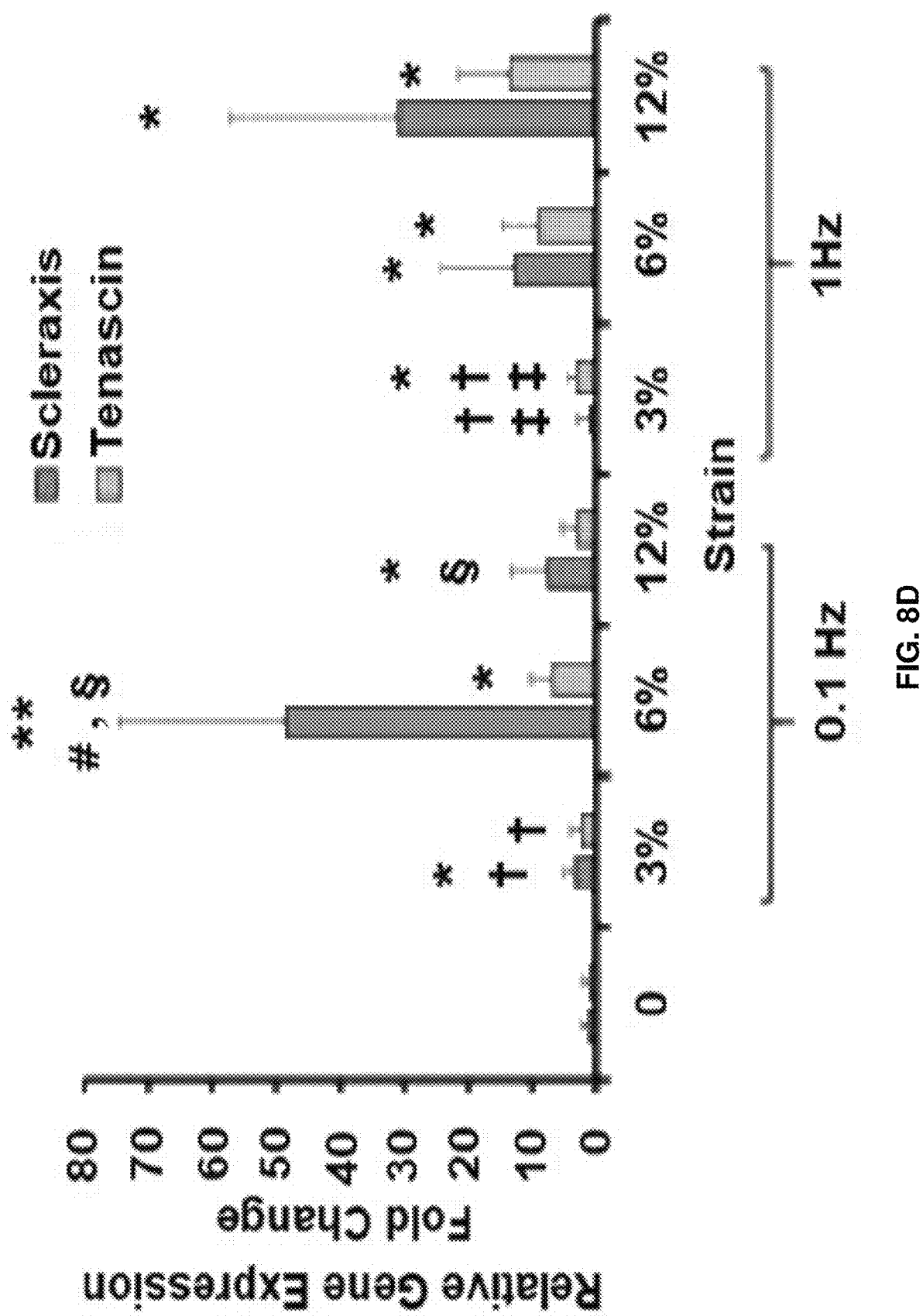
Figure 8E:
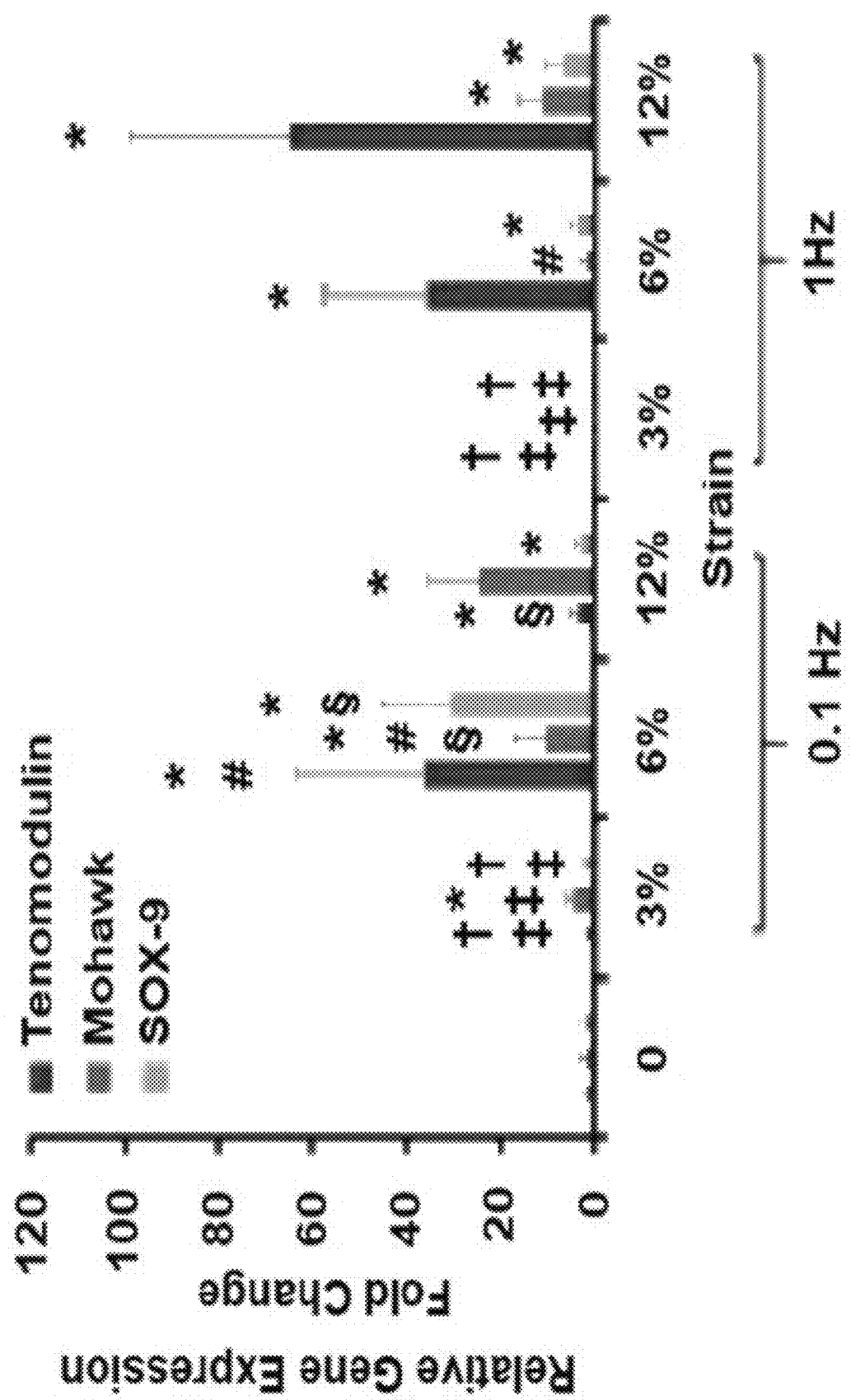

It has been demonstrated that aligned collagen type-I fibers within cell-embedded collagen matrix with a degree of alignment of 95% can be created using mechanical loading platforms and the laden-cells can be kept alive and functioning for over a month (FIG. 7). Collagen fiber alignment (top row in FIG. 7) was evaluated by scanning electron microscopy (SEM). Residing cells within the collagen matrices were visualized by confocal microscopy (bottom row in FIG. 7) by labeling cells with calcein-AM to illustrate live cells. Scale bar=100 μm.

Changes in Gene Expressions Due to Cyclic Mechanical Loading

Cellular three-dimensional scaffolds were prepared by encapsulating the desired cell line within neutralized 3 mg/ml collagen type-I solution (Corning Life Sciences) at $1\times10^6$ cells/ml seeding density, 0.75 ml was added into the mechanical loading chamber, and the scaffold was allowed to polymerize. 1 ml of cell growth media was added into the well of each loading chamber once the scaffold was polymerized and stored in a cell culture incubator at 37° C. for 48 hours. The scaffolds were then subjected to cyclic stretching using the mechanical loading platform at the desired strain, frequency, and duration of loading. The loading apparatus was placed in the incubator during its operation, thus ensuring that the cells within the scaffold continued to remain in their preferred environment. Media in the well was replenished every 3-4 days. Scaffolds subjected to no loading (unstrained) were used as control samples. The scaffolds were harvested at the end of the experiment. The gene expression of the cells was analyzed using Real-time Polymerized Chain Reaction (RT-PCR).

Various kinds of genes were analyzed under different mechanical loading strains from 0% to 12% under 1 Hz and 0.1 Hz frequency. FIGS. 8A-8E shows the changes in gene expressions after mechanical loading. The gene expression profiles for the ECM proteins as well as AF markers were upregulated by equiaxial mechanical loading.

Certain embodiments of the devices and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the devices and methods described herein to various usages and conditions. Various changes may be made, and equivalents may be substituted for elements thereof without departing from the essential scope of the disclosure. In addition, many modifications may be made to adapt a particular situation or material to the teachings of the disclosure without departing from the essential scope thereof.

What is claimed is:

1. An adjustable gravity simulator comprising:
  a simulator chamber configured to house a sample and rotate independently around a first axis and a second axis;
  a rotating arm rotatably connected to a mount and having side members extending toward the simulator chamber, wherein rotation of the rotating arm around the first axis in turn causes rotation of the simulator chamber around the first axis;
  a belt tensioner on one of the side members and connected to the simulator chamber, wherein the belt tensioner comprises a belt configured to move in a loop thereby driving the rotation of the simulator chamber around the second axis; and
  one or more motors configured to drive (i) the rotation of the rotating arm around the first axis, and thereby the rotation of the simulator chamber around the first axis, and (ii) movement of the belt in the loop, and thereby the rotation of the simulator chamber around the second axis.

2. The adjustable gravity simulator of claim 1, wherein the one or more motors comprises a first motor configured to drive the rotation of the rotating arm relative to the mount, and a second motor configured to drive the movement of the belt in the loop.

3. The adjustable gravity simulator of claim 1, further comprising a control module configured to control the one or more motors.

4. The adjustable gravity simulator of claim 1, wherein the mount comprises a wheel and a cable, wherein rotation of the wheel by movement of the cable causes corresponding rotation of the rotating arm around the first axis, and wherein movement of the cable is driven by a first motor.

5. The adjustable gravity simulator of claim 1, wherein the mount is disposed on a base defining a surface and extends orthogonally from the surface.

6. The adjustable gravity simulator of claim 1, further comprising a second motor configured to drive rotation of an arm wheel in the loop, and thereby drive movement of the belt in the loop, rotation of the chamber wheel, and rotation of the simulator chamber around the second axis.

7. The adjustable gravity simulator of claim 1, further comprising a (Original) mechanical loading device within the simulator chamber, wherein the mechanical loading device is configured to apply a mechanical load to a sample housed therein.

8. The adjustable gravity simulator of claim 7, further comprising one or more slip rings configured to provide electricity to the mechanical loading device within the simulator chamber.

9. The adjustable gravity simulator of claim 7, wherein the mechanical loading device comprises a loading chamber configured to house a sample and a third motor configured to apply a mechanical load to the sample in the loading chamber.

10. The adjustable gravity simulator of claim 9, wherein the third motor is configured to move the sample axially along a third axis in a back-and-forth manner.

11. The adjustable gravity simulator of claim 9, wherein the loading chamber is interchangeable and autoclavable.

12. The adjustable gravity simulator of claim 7, wherein the mechanical loading device comprises a loading plate configured to receive and support a sample or culturing chamber, and the mechanical loading device further comprises a third motor configured to move the loading plate axially along a third axis in a back-and-forth manner.

13. The adjustable gravity simulator of claim 1, wherein movement of the belt in the loop drives rotation of a chamber wheel, and rotation of the chamber wheel in turn drives rotation of the simulator chamber around the second axis.

14. The adjustable gravity simulator of claim 1, wherein the side members extend from a side of the rotating arm opposing the mount and facing the simulator chamber.

15. The adjustable gravity simulator of claim 1, further comprising an accelerometer configured to collect gravitational data.

16. The adjustable gravity simulator of claim 1, comprising a first motor and a second motor, wherein:
  the first motor is configured to drive movement of a cable around a wheel which causes corresponding rotation of the rotating arm around the first axis, and thereby drives rotation of the simulator chamber around the first axis; and
  the second motor is configured to drive movement of the belt in the loop, and thereby drive rotation of an arm wheel in the loop which, in turn, causes corresponding rotation of the simulator chamber around the second axis.

* * * * *